(12) United States Patent
Evans et al.

(10) Patent No.: US 8,283,345 B2
(45) Date of Patent: Oct. 9, 2012

(54) AZETIDINE ANALOGUES OF NUCLEOSIDASE AND PHOSPHORYLASE INHIBITORS

(75) Inventors: Gary Brian Evans, Lower Hutt (NZ); Richard Hubert Furneaux, Wellington (NZ); Ben William Greatrex, Armidale (AU); Vern L. Schramm, New Rochelle, NY (US); Peter Charles Tyler, Wellington (NZ)

(73) Assignees: Industrial Research Limited, Lower Hutt (NZ); Albert Einstein College of Medicine of Yeshiva University, Bronx, NY (US)

( * ) Notice: Subject to any disclaimer, the term of this patent is extended or adjusted under 35 U.S.C. 154(b) by 293 days.

(21) Appl. No.: 12/448,397

(22) PCT Filed: Dec. 21, 2007

(86) PCT No.: PCT/NZ2007/000387
§ 371 (c)(1),
(2), (4) Date: Feb. 23, 2010

(87) PCT Pub. No.: WO2008/079028
PCT Pub. Date: Jul. 3, 2008

(65) Prior Publication Data
US 2010/0168141 A1 Jul. 1, 2010

Related U.S. Application Data

(60) Provisional application No. 60/876,947, filed on Dec. 22, 2006.

(51) Int. Cl.
*A01N 43/00* (2006.01)
*A01N 43/90* (2006.01)
*A61K 31/00* (2006.01)
*A61K 31/519* (2006.01)
*C07D 487/00* (2006.01)

(52) U.S. Cl. ............... 514/210.21; 514/265.1; 544/280

(58) Field of Classification Search ................. None
See application file for complete search history.

(56) References Cited

U.S. PATENT DOCUMENTS

| | | | |
|---|---|---|---|
| 5,985,848 A | 11/1999 | Furneaux et al. |
| 6,066,722 A | 5/2000 | Furneaux et al. |
| 6,140,347 A | 10/2000 | Pineiro et al. |
| 6,228,847 B1 | 5/2001 | Furneaux et al. |
| 6,281,243 B1 | 8/2001 | Leysen et al. |
| 6,379,911 B2 | 4/2002 | Schramm et al. |
| 6,458,799 B1 | 10/2002 | Montgomery et al. |
| 6,492,347 B2 | 12/2002 | Furneaux et al. |
| 6,693,193 B1 | 2/2004 | Furneaux et al. |
| 6,764,829 B2 | 7/2004 | Schramm et al. |
| 6,803,455 B2 | 10/2004 | Furneaux et al. |
| 7,022,852 B2 | 4/2006 | Furneaux et al. |
| 7,098,334 B2 | 8/2006 | Furneaux et al. |
| 7,109,331 B2 | 9/2006 | Furneaux et al. |
| 7,211,653 B2 | 5/2007 | Furneaux et al. |
| 7,211,677 B2 | 5/2007 | Furneaux et al. |
| 7,390,890 B2 | 6/2008 | Furneaux et al. |
| 7,405,297 B2 | 7/2008 | Furneaux et al. |
| 7,553,839 B2 | 6/2009 | Evans et al. |
| 7,655,795 B2 | 2/2010 | Evans et al. |
| 2006/0058284 A1 | 3/2006 | Yang et al. |
| 2006/0160765 A1 | 7/2006 | Evans et al. |
| 2006/0217551 A1 | 9/2006 | Evans et al. |
| 2007/0275988 A1 | 11/2007 | Schramm |
| 2008/0280334 A1 | 11/2008 | Lenz et al. |
| 2009/0233948 A1 | 9/2009 | Evans et al. |
| 2009/0239885 A1 | 9/2009 | Evans et al. |
| 2009/0325986 A1 | 12/2009 | Furneaux et al. |
| 2010/0062995 A1 | 3/2010 | Schramm |
| 2010/0094003 A1 | 4/2010 | Evans et al. |
| 2010/0222370 A1 | 9/2010 | Schramm et al. |
| 2011/0046167 A1 | 2/2011 | Clinch et al. |

FOREIGN PATENT DOCUMENTS
WO        0061783       10/2000
(Continued)

OTHER PUBLICATIONS

Wolff et. al., "Burger's Medicinal Chemistry and Drug Discovery," 5th Ed. Part 1, pp. 975-977 (1995).*

(Continued)

*Primary Examiner* — Jeffrey Murray
(74) *Attorney, Agent, or Firm* — Amster, Rothstein & Ebenstein LLP

(57) ABSTRACT

Disclosed are azetidine analogues of nucleosidase and nucleoside phosphorylase inhibitors, the use of these compounds as pharmaceuticals, pharmaceutical compositions containing the compounds, methods of treating certain diseases using the compounds, processes for preparing the compounds, and intermediates useful in the preparation of the compounds.

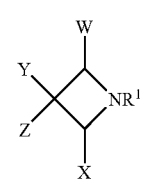

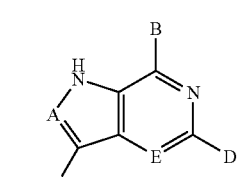

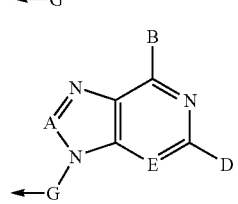

22 Claims, 2 Drawing Sheets

FOREIGN PATENT DOCUMENTS

| | | |
|---|---|---|
| WO | 0218371 | 3/2002 |
| WO | 03080620 | 10/2003 |
| WO | 2004018496 | 3/2004 |
| WO | 2005118532 | 12/2005 |
| WO | 2006014913 | 2/2006 |
| WO | 2006123953 | 11/2006 |
| WO | 2007016291 | 2/2007 |
| WO | 2007069923 | 6/2007 |
| WO | 2007097647 | 8/2007 |
| WO | 2007097648 | 8/2007 |
| WO | 2008030118 | 3/2008 |
| WO | 2008030119 | 3/2008 |
| WO | 2008039324 | 4/2008 |
| WO | 2009082247 A1 | 7/2009 |
| WO | 2010033236 A2 | 2/2010 |
| WO | 2011008110 A1 | 1/2011 |

OTHER PUBLICATIONS

Banker, et. al., (1996), Modern Pharmaceuticals, p. 596.*

Communication Supplementary European Search Report dated Sep. 21, 2010 received from the European Patent Office in connection with European Patent Application No. 07866894.4, 5 pages.

PCT Notification Concerning Transmittal of International Preliminary Report on Patentability dated Jul. 2, 2009 in connection with PCT International Patent Application No. PCT/NZ2007/000387, 2 pages.

Written Opinion of the International Searching Authority dated Apr. 16, 2008 in connection with PCT International Patent Application No. PCT/NZ2007/000387, 5 pages.

Kato, K et al., entitled "Synthesis of Nucleosides Having Unusual Branched Sugars As Potential Antiviral Agents," Nucleosides & Nucleotides, 18(4&5), 657-658 (1999).

Nishiyama, S et al., entitled "Enantiomerically Pure Synthesis and Antiviral Evaluation of [(2'S, 3'S)-Bis (Hydroxymethyl)Azetidin-1-YL] Purine Nucleosides: Analogs of Oxetanocin-A", Bioorganic & Medicinal Chemistry Letters, vol. 5, No. 19, 2273-2276, (1995).

Hulin, B et al., entitled "New fluorinated pyrrolidine and azetidine amides as dipeptidyl peptidase IV inhibitors," Bioorganic & Medicinal Chemistry Letters 15, 4770-4773, (2005).

US 6,281,343, 08/2001, Leysen et al. (withdrawn)

* cited by examiner

AZETIDINE ANALOGUES OF NUCLEOSIDASE AND PHOSPHORYLASE INHIBITORS

CROSS-REFERENCE TO RELATED APPLICATIONS

This application is a national stage entry under 35 U.S.C. §371 of PCT International Patent Application No. PCT/NZ2007/000387, filed Dec. 21, 2007, and claims priority to U.S. Provisional Patent Application No. 60/876,947, filed Dec. 22, 2006, the contents of which are incorporated herein by reference in their entirety.

STATEMENT OF GOVERNMENT SUPPORT

This invention was made with government support under grant number GM41916 awarded by from the National Institutes of Health, U.S. Department of Health and Human Services. The government has certain rights in the invention.

TECHNICAL FIELD

This invention relates to certain azetidine analogues of nucleosidase and nucleoside phosphorylase inhibitors, the use of these compounds as pharmaceuticals, pharmaceutical compositions containing the compounds, methods of treating certain diseases using the compounds, processes for preparing the compounds, and intermediates useful in the preparation of the compounds.

BACKGROUND

Recent research in the area of purine nucleoside phosphorylase (PNP), methylthioadenosine phosphorylase (MTAP), 5'-methylthioadenosine nucleosidase (MTAN), and nucleoside hydrolase inhibitors has resulted in the design of a class of compounds known as the Immucillins, some of which are potent inhibitors of one or more of the above enzymes. Immucillins are nucleoside analogues where the "sugar" part of the molecule has been replaced with an "imino sugar" moiety.

PNP catalyses the phosphorolytic cleavage of the ribo- and deoxyribonucleosides of guanine and hypoxanthine to give the corresponding sugar-1-phosphate and guanine, hypoxanthine, or other purine bases.

Humans deficient in PNP suffer a specific T-cell immunodeficiency due to an accumulation of dGTP which prevents stimulation of T lymphocytes. Inhibitors of PNP are therefore immunosuppressive, and are active against T-cell malignancies and T-cell proliferative disorders.

U.S. Pat. No. 5,985,848, U.S. Pat. No. 6,066,722 and U.S. Pat. No. 6,228,741 describe compounds known as Immucillins that are inhibitors of PNP and purine phosphoribosyltransferases (PPRT). These Immucillins are useful for treating parasitic infections, T-cell malignancies, autoimmune diseases and inflammatory disorders. They are also useful for immunosuppression in organ transplantation.

U.S. Pat. No. 6,693,193 and U.S. Pat. No. 7,022,852 describe a process for preparing certain Immucillin compounds, providing another useful route to the synthesis of this class of compounds. U.S. Pat. No. 7,109,331 discloses further Immucillins that are inhibitors of PNP and PPRT.

The imino sugar part of an Immucillin molecule has the nitrogen atom located between C-1 and C-4 so as to form a 1,4-dideoxy-1,4-imino-D-ribitol compound. The location of the nitrogen atom in the ribitol ring may be important for binding to enzymes. In addition, the location of the link between the imino sugar moiety and the nucleoside base analogue may be critical for enzyme inhibitory activity. The compounds described above have that link at C-1 of the imino sugar ring.

Another related class of nucleoside phosphorylase and nucleosidase inhibitor compounds, known as DAD-Me-Immucillins, has been developed. The location of the nitrogen atom in the imino sugar ring of this class of compounds is varied and/or the imino sugar moiety is linked to the nucleoside base analogue via a methylene bridge. DAD-Me-Immucillins are described in U.S. Ser. No. 10/524,995.

Some of the Immucillins have also been identified as potent inhibitors of MTAP and MTAN. These are the subject of U.S. Ser. No. 10/395,636. MTAP and MTAN function in the polyamine biosynthesis pathway, in purine salvage in mammals, and in the quorum sensing pathways in bacteria. MTAP catalyses the reversible phosphorolysis of MTA to adenine and 5-methylthio-α-D-ribose-1-phosphate (MTR-1P). MTAN catalyses the reversible hydrolysis of MTA to adenine and 5-methylthio-α-D-ribose, and the reversible hydrolysis of S-adenosyl-L-homocysteine (SAH) to adenine and S-ribosyl-homocysteine (SRH). The adenine formed is subsequently recycled and converted into nucleotides. The only source of free adenine in the human cell is a result of the action of these enzymes. The MTR-1 P is subsequently converted into methionine by successive enzymatic actions.

MTA is a by-product of the reaction involving the transfer of an aminopropyl group from decarboxylated S-adenosyl-methionine to putrescine during the formation of spermidine. The reaction is catalyzed by spermidine synthase. Likewise, spermine synthase catalyses the conversion of spermidine to spermine, with concomitant production of MTA as a by-product. Spermidine synthase is very sensitive to product inhibition by accumulation of MTA. Therefore, inhibition of MTAP or MTAN severely limits the polyamine biosynthesis and the salvage pathway for adenine in the cells.

MTA is also the by-product of the bacterial synthesis of acylated homoserine lactones from S-adenosylmethionine (SAM) and acyl-acyl carrier proteins in which the subsequent lactonization causes release of MTA and the acylated homoserine lactone. The acylated homoserine lactone is a bacterial quorum sensing molecule in bacteria that is involved in bacterial virulence against human tissues. The homoserine lactone pathway will suffer feedback inhibition by the accumulation of MTA.

MTAP deficiency due to a genetic deletion has been reported with many malignancies. The loss of MTAP enzyme function in these cells is known to be due to homozygous deletions on chromosome 9 of the closely linked MTAP and p16/MTS1 tumour suppressor gene. As the absence of p16/MTS1 is probably responsible for the tumour, the lack of MTAP activity is a consequence of the genetic deletion and is not causative for the cancer. However, the absence of MTAP alters the purine metabolism in these cells so that they are mainly dependent on the de novo pathway for their supply of purines.

MTAP inhibitors are also expected to be very effective against parasitic infections, such as malaria which infects red blood cells (RBCs), because such infections lack the de novo pathway for purine biosynthesis. Protozoan parasites depend entirely upon the purines produced by the salvage pathway for their growth and propagation. MTAP inhibitors will therefore kill these parasites without having any negative effect on the host RBCs, because RBCs are terminally differentiated cells and they do not synthesize purines, produce polyamines or multiply.

MTA has been shown to induce apoptosis in dividing cancer cells, but to have the opposite, anti-apoptotic effect on dividing normal cells such as hepatocytes (E. Ansorena et al., Hepatology, 2002, 35: 274-280). Administration of MTA in circumstances where its degradation by MTAP is inhibited by an MTAP inhibitor will lead to greater circulatory and tissue levels of MTA and consequently an enhanced effect in the treatment of cancer.

MTAP and MTAN inhibitors may therefore be used in the treatment of diseases such as cancer, bacterial infections or protozoal parasitic infections, where it is desirable to inhibit MTAP or MTAN. Such treatments are described in U.S. Ser. No. 10/395,636 and U.S. Ser. No. 10/524,995.

The Immucillins and DAD-Me-Immucillins are also useful as inhibitors of nucleoside hydrolases. These enzymes catalyse the hydrolysis of nucleosides. They are not found in mammals, but are required for nucleoside salvage in some protozoan parasites. Certain protozoan parasites use nucleoside phosphorylases instead of, or as well as, nucleoside hydrolases for this purpose. Inhibitors of nucleoside hydrolases and phosphorylases can be expected to interfere with the metabolism of the parasite and therefore be usefully employed against protozoan parasites.

The X-ray crystal structure of one of the inhibitor compounds (DAD-Me-Immucillin-H) bound to *Mycobacterium tuberculosis* PNP has been described (A. Lewandowicz, W. Shi, G. B. Evans, P. C. Tyler, R. H. Furneaux, L. A. Basso, D. S. Santos, S. C. Almo and V. L. Schramm, Biochemistry, 42 (2003) 6057-6066.). The complex of this inhibitor with PNP has favourable hydrogen bonds to almost every hydrogen bond donor-acceptor site in the complex. Even a slight structural change can disrupt this favourable hydrogen bonding pattern, as demonstrated by energetic mapping of transition state analogue interactions with human and *Plasmodium falciparum* PNPs (A. Lewandowicz, E. A. T. Ringia, L.-M. Ting, K. Kim, P. C. Tyler, G. B. Evans, O. V. Zubkova, S. Mee, G. F. Painter, D. H. Lenz, R. H. Furneaux and V. L. Schramm, J. Biol. Chem., 280 (2005) 30320-30328).

It was previously considered that, in view of the importance of hydrogen bonding and the location of chemical moieties in the donor-acceptor site, an inhibitor of these enzymes would likely require the imino sugar moiety to have a 5-membered ring and to have chirality at certain locations. However, in the ongoing search for new and improved nucleoside phosphorylase and nucleosidase inhibitors, the applicants found that azetidine analogues of Immucillins and DAD-Me-Immucillins, which have a 4-membered ring as the imino-sugar analogue, some of which are achiral, are surprisingly potent inhibitors of at least one of PNP, PPRT, MTAP and MTAN. The 4-membered ring of the azetidine would not have been expected to orient functional substituents such as hydroxyl-groups in orientations close enough to effectively participate in the hydrogen-bonding networks considered responsible for the potent inhibition observed for the Immucillins and DAD-Me-Immucillins.

It is therefore an object of the present invention to provide novel inhibitors of PNP, PPRT, MTAP, MTAN, and/or nucleoside hydrolases, or to at least provide a useful choice.

STATEMENTS OF INVENTION

In a first aspect the invention provides a compound of formula (I):

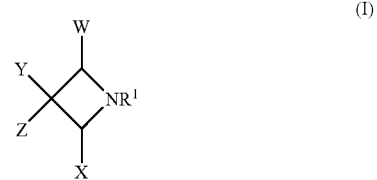

wherein:
W and X are each independently selected from hydrogen, $CH_2OH$, $CH_2OQ$ and $CH_2SQ$;
Y and Z are each independently selected from hydrogen, halogen, $CH_2OH$, $CH_2OQ$, $CH_2SQ$, SQ, OQ and Q;
Q is an alkyl, aralkyl or aryl group each of which may be optionally substituted with one or more substituents selected from hydroxy, halogen, methoxy, amino, or carboxy;
$R^1$ is a radical of the formula (II)

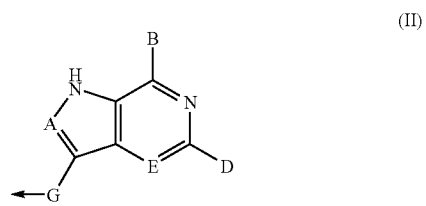

or $R^1$ is a radical of the formula (III)

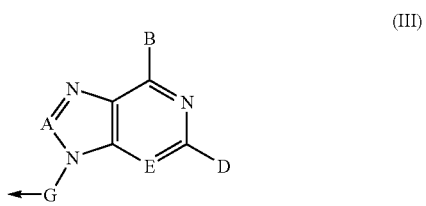

A is selected from N, CH and $CR^2$, where $R^2$ is selected from halogen, alkyl, aralkyl, aryl, OH, $NH_2$, $NHR^3$, $NR^3R^4$ and $SR^5$, where $R^3$, $R^4$ and $R^5$ are each alkyl, aralkyl or aryl groups optionally substituted with hydroxy or halogen, and where $R^2$ is optionally substituted with hydroxy or halogen when $R^2$ is alkyl, aralkyl or aryl;
B is selected from hydroxy, $NH_2$, $NHR^6$, SH, hydrogen and halogen, where $R^6$ is an alkyl, aralkyl or aryl group optionally substituted with hydroxy or halogen;
D is selected from hydroxy, $NH_2$, $NHR^7$, hydrogen, halogen and $SCH_3$, where $R^7$ is an alkyl, aralkyl or aryl group optionally substituted with hydroxy or halogen;
E is selected from N and CH;
G is a $C_{1-4}$ saturated or unsaturated alkyl group optionally substituted with hydroxy or halogen, or G is absent;
or a tautomer thereof, or a pharmaceutically acceptable salt thereof, or an ester thereof, or a prodrug thereof.

Preferably Z is selected from hydrogen, halogen, $CH_2OH$, $CH_2OQ$ and $CH_2SQ$. More preferably Z is $CH_2OH$. Alternatively it is preferred that Z is $CH_2SQ$. In another preferred embodiment, Z is Q.

It is preferred that G is $CH_2$.

$R^1$ may be a radical of the formula (II) or, alternatively, may be a radical of formula (III).

Preferred compounds of the invention include those where one of Y and Z is $CH_2OQ$ and the other is hydrogen.

Other preferred compounds of the invention include those where one of Y and Z is $CH_2SQ$ and the other is hydrogen.

B is preferably hydroxy or $NH_2$. A is preferably CH or N. D is preferably H or $NH_2$. It is also preferred that E is N.

It is preferred that when any of Y, Z, B and D is halogen, each halogen is independently chlorine or fluorine.

Preferred compounds of the invention include:
i. meso-7-((2,4-cis-2,4-bis(hydroxymethyl)azetidin-1-yl)methyl)-3H-pyrrolo[3,2-d]pyrimidin-4(5H)-one;
ii. (±)7-((2,4-trans-2,4-bis(hydroxymethyl)azetidin-1-yl)methyl)-3H-pyrrolo[3,2-d]pyrimidin-4(5H)-one;
iii. (+)7-((2,4-trans-2,4-bis(hydroxymethyl)azetidin-1-yl)methyl)-3H-pyrrolo[3,2-d]pyrimidin-4(5H)-one;
iv. (−)7-(4-trans-2,4-bis(hydroxymethyl)azetidin-1-yl)methyl)-3H-pyrrolo[3,2-d]pyrimidin-4(5H)-one;
v. 7-((3,3-bis(hydroxymethyl)azetidin-1-yl)methyl)-3H-pyrrolo[3,2-d]pyrimidin-4(5H)-one;
vi. (±)7-((2-(hydroxymethyl)azetidin-1-yl)methyl)-3H-pyrrolo[3,2-d]pyrimidin-4(5H)-one;
vii. 7-(((2R)-2-(hydroxymethyl)azetidin-1-yl)methyl)-3H-pyrrolo[3,2-d]pyrimidin-4(5H)-one;
viii. 7-(((2S)-2-(hydroxymethyl)azetidin-1-yl)methyl)-3H-pyrrolo[3,2-d]pyrimidin-4(5H)-one;
ix. 7-((3-(hydroxymethyl)azetidin-1-yl)methyl)-3H-pyrrolo[3,2-d]pyrimidin-4(5H)-one;
x. 7-((3-hydroxy-3-(hydroxymethyl)azetidin-1-yl)methyl)-3H-pyrrolo[3,2-d]pyrimidin-4(5H)-one;
xi. (±)7-((2,3-cis-3-hydroxy-2-(hydroxymethyl)azetidin-1-yl)methyl)-3H-pyrrolo[3,2-d]pyrimidin-4(5H)-one;
xii. (+)7-((2,3-cis-3-hydroxy-2-(hydroxymethyl)azetidin-1-yl)methyl)-3H-pyrrolo[3,2-d]pyrimidin-4(5H)-one;
xiii. (−)7-((2,3-cis-3-hydroxy-2-(hydroxymethyl)azetidin-1-yl)methyl)-3H-pyrrolo[3,2-d]pyrimidin-4(5H)-one;
xiv. (±)7-((2,3-trans-3-hydroxy-2-(hydroxymethyl)azetidin-1-yl)methyl)-3H-pyrrolo[3,2-d]pyrimidin-4(5H)-one;
xv. (+)7-((2,3-trans-3-hydroxy-2-(hydroxymethyl)azetidin-1-yl)methyl)-3H-pyrrolo[3,2-d]pyrimidin-4(5H)-one;
xvi. (−)7-((2,3-trans-3-hydroxy-2-(hydroxymethyl)azetidin-1-yl)methyl)-3H-pyrrolo[3,2-d]pyrimidin-4(5H)-one;
xvii. meso-2-amino-7-((2,4-cis-2,4-bis(hydroxymethyl)azetidin-1-yl)methyl)-3H-pyrrolo[3,2-d]pyrimidin-4(5H)-one;
xviii. (±)2-amino-7-((2,4-trans-2,4-bis(hydroxymethyl)azetidin-1-yl)methyl)-3H-pyrrolo[3,2-d]pyrimidin-4(5H)-one;
xix. (+)2-amino-7-((2,4-trans-2,4-bis(hydroxymethyl)azetidin-1-yl)methyl)-3H-pyrrolo[3,2-d]pyrimidin-4(5H)-one;
xx. (−)2-amino-7-((2,4-trans-2,4-bis(hydroxymethyl)azetidin-1-yl)methyl)-3H-pyrrolo[3,2-d]pyrimidin-4(5H)-one;
xxi. 2-amino-7-((3,3-bis(hydroxymethyl)azetidin-1-yl)methyl)-3H-pyrrolo[3,2-d]pyrimidin-4(5H)-one;
xxii. (±)2-amino-7-((2-(hydroxymethyl)azetidin-1-yl)methyl)-3H-pyrrolo[3,2-d]pyrimidin-4(5H)-one;
xxiii. 2-amino-7-(((2R)-2-(hydroxymethyl)azetidin-1-yl)methyl)-3H-pyrrolo[3,2-d]pyrimidin-4(5H)-one;
xxiv. 2-amino-7-(((2S)-2-(hydroxymethyl)azetidin-1-yl)methyl)-3H-pyrrolo[3,2-d]pyrimidin-4(5H)-one;
xxv. 2-amino-7-((3-(hydroxymethyl)azetidin-1-yl)methyl)-3H-pyrrolo[3,2-d]pyrimidin-4(5H)-one;
xxvi. 2-amino-7-((3-hydroxy-3-(hydroxymethyl)azetidin-1-yl)methyl)-3H-pyrrolo[3,2-d]pyrimidin-4(5H)-one;
xxvii. (±)2-amino-7-((2,3-trans-3-hydroxy-2-(hydroxymethyl)azetidin-1-yl)methyl)-3H-pyrrolo[3,2-d]pyrimidin-4(5H)-one;
xxviii. (−)2-amino-7-((2,3-trans-3-hydroxy-2-(hydroxymethyl)azetidin-1-yl)methyl)-3H-pyrrolo[3,2-d]pyrimidin-4(5H)-one;
xxix. (+)2-amino-7-((2,3-trans-3-hydroxy-2-(hydroxymethyl)azetidin-1-yl)methyl)-3H-pyrrolo[3,2-d]pyrimidin-4(5H)-one;
xxx. (±)2-amino-7-((2,3-cis-3-hydroxy-2-(hydroxymethyl)azetidin-1-yl)methyl)-3H-pyrrolo[3,2-d]pyrimidin-4(5H)-one;
xxxi. (+)2-amino-7-((2,3-cis-3-hydroxy-2-(hydroxymethyl)azetidin-1-yl)methyl)-3H-pyrrolo[3,2-d]pyrimidin-4(5H)-one;
xxxii. (−)2-amino-7-((2,3-cis-3-hydroxy-2-(hydroxymethyl)azetidin-1-yl)methyl)-3H-pyrrolo[3,2-d]pyrimidin-4(5H)-one;
xxxiii. (1-((4-amino-5H-pyrrolo[3,2-d]pyrimidin-7-yl)methyl)-3-(methylthiomethyl)azetidin-3-yl)methanol;
xxxiv. 1-((4-amino-5H-pyrrolo[3,2-d]pyrimidin-7-yl)methyl)-3-(methylthiomethyl)azetidin-3-ol;
xxxv. (±)-(2,4-trans-1-((4-amino-5H-pyrrolo[3,2-d]pyrimidin-7-yl)methyl)-4-(methylthiomethyl)azetidin-2-yl)methanol;
xxxvi. (+)-(2,4-trans-1-((4-amino-5H-pyrrolo[3,2-d]pyrimidin-7-yl)methyl)-4-(methylthiomethyl)azetidin-2-yl)methanol;
xxxvii. (−)-(2,4-trans-1-((4-amino-5H-pyrrolo[3,2-d]pyrimidin-7-yl)methyl)-4-(methylthiomethyl)azetidin-2-yl)methanol;
xxxviii. meso-(2,4-cis-1-((4-amino-5H-pyrrolo[3,2-d]pyrimidin-7-yl)methyl)-4-(methylthiomethyl)azetidin-2-yl)methanol;
xxxix. 7-(((2RS)-2-(methylthiomethyl)azetidin-1-yl)methyl)-5H-pyrrolo[3,2-d]pyrimidin-4-amine;
xl. 7-(((2R)-2-(methylthiomethyl)azetidin-1-yl)methyl)-5H-pyrrolo[3,2-d]pyrimidin-4-amine;
xli. 7-(((2S)-2-(methylthiomethyl)azetidin-1-yl)methyl)-5H-pyrrolo[3,2-d]pyrimidin-4-amine;
xlii. 7-((3-(methylthiomethyl)azetidin-1-yl)methyl)-5H-pyrrolo[3,2-d]pyrimidin-4-amine; and
xliii. (±)2,3-trans-1-((4-amino-5H-pyrrolo[3,2-d]pyrimidin-7-yl)methyl)-2-(methylthiomethyl)azetidin-3-ol.
xliv. (+)2,3-trans-1-((4-amino-5H-pyrrolo[3,2-d]pyrimidin-7-yl)methyl)-2-(methylthiomethyl)azetidin-3-ol.
xlv. (−)2,3-trans-1-((4-amino-5H-pyrrolo[3,2-d]pyrimidin-7-yl)methyl)-2-(methylthiomethyl)azetidin-3-ol.
xlvi. (±)2,3-cis-1-((4-amino-5H-pyrrolo[3,2-d]pyrimidin-7-yl)methyl)-2-(methylthiomethyl)azetidin-3-ol.
xlvii. (+)2,3-cis-1-((4-amino-5H-pyrrolo[3,2-d]pyrimidin-7-yl)methyl)-2-(methylthiomethyl)azetidin-3-ol.
xlviii. (−)2,3-cis-1-((4-amino-5H-pyrrolo[3,2-d]pyrimidin-7-yl)methyl)-2-(methylthiomethyl)azetidin-3-ol.

According to another aspect of the invention, there is provided a pharmaceutical composition comprising a pharmaceutically effective amount of a compound of the formula (I).

Preferably the pharmaceutical composition comprises one of the above preferred compounds of the invention.

In another aspect of the invention there is provided a method of treating or preventing diseases or conditions in which it is desirable to inhibit PNP comprising administering a pharmaceutically effective amount of a compound of formula (I) to a patient requiring treatment. The diseases or conditions include cancer, bacterial and parasitic infections, and T-cell mediated diseases such as psoriasis, lupus, arthritis and other autoimmune diseases. This aspect of the invention also includes use of the compounds for immunosuppression for organ transplantation. Preferably the compound is one of the above preferred compounds of the invention.

The parasitic infections include those caused by protozoan parasites such as those of the genera *Giardia, Trichomonas, Leishmania, Trypanosome, Crithidia, Herpetomonas, Leptomonas, Histomonas, Eimeria, Isopora* and *Plasmodium*. The method can be advantageously applied with any parasite containing one or more nucleoside hydrolases inhibited by a compound of the invention when administered in an amount providing an effective concentration of the compound at the location of the enzyme.

In another aspect, the invention provides a method of treating or preventing diseases or conditions in which it is desirable to inhibit MTAP comprising administering a pharmaceutically effective amount of a compound of formula (I) to a patient requiring treatment. The diseases include cancer, for example prostate and head and neck tumours.

In another aspect, the invention provides a method of treating or preventing diseases or conditions in which it is desirable to inhibit MTAN comprising administering a pharmaceutically effective amount of a compound of formula (I) to a patient requiring treatment. The diseases include bacterial infections.

In another aspect the invention provides the use of a compound of formula (I) for the manufacture of a medicament for treating one or more of these diseases or conditions.

In a further aspect of the invention there is provided a method of preparing a compound of formula (I).

DETAILED DESCRIPTION

Definitions

Figure 1:
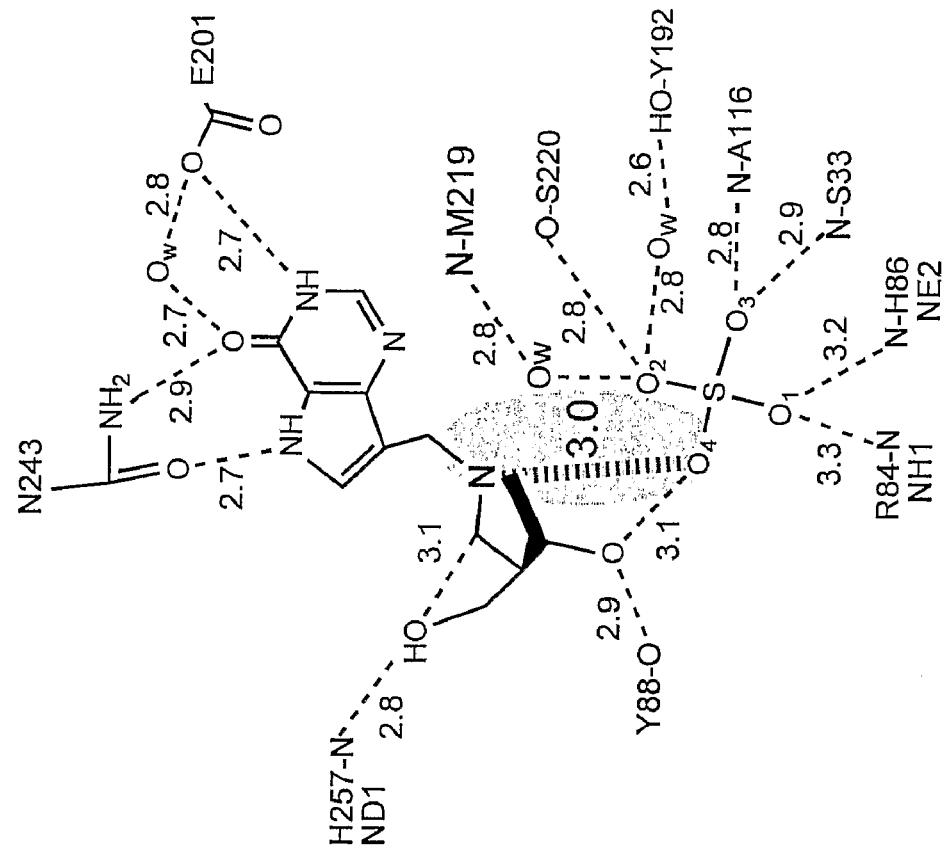
FIG. 1 shows human PNP catalytic sites with Immucillin-H and DADMe-Immucillin-H.
Figure 1:
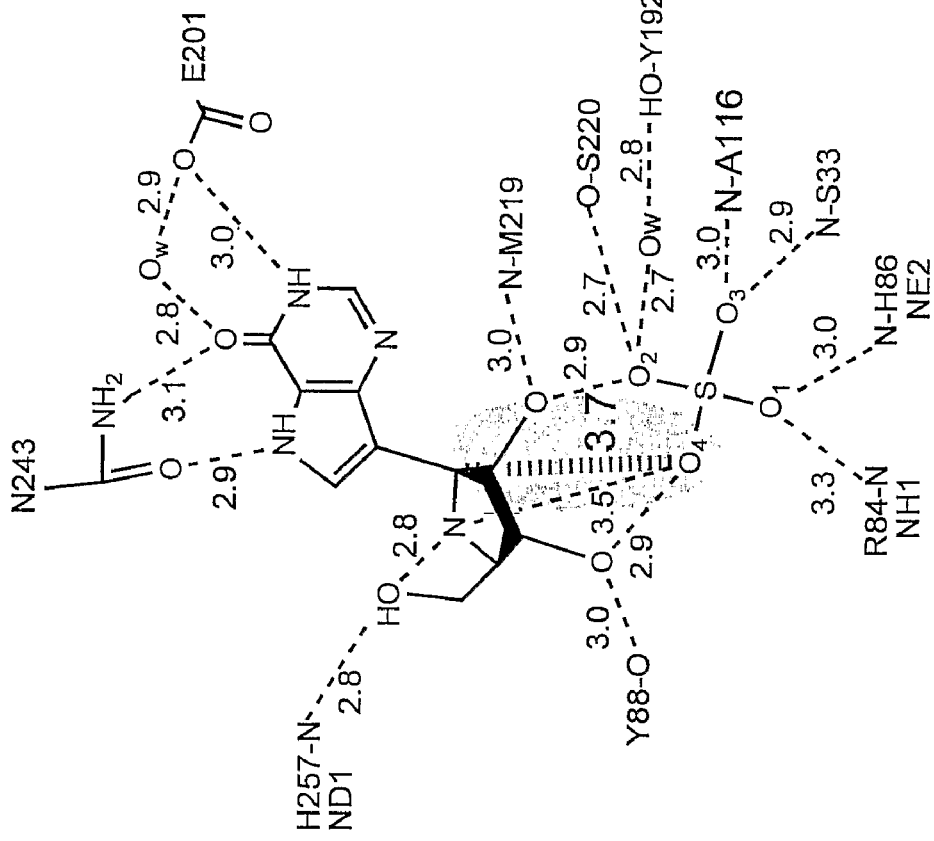
Figure 2:
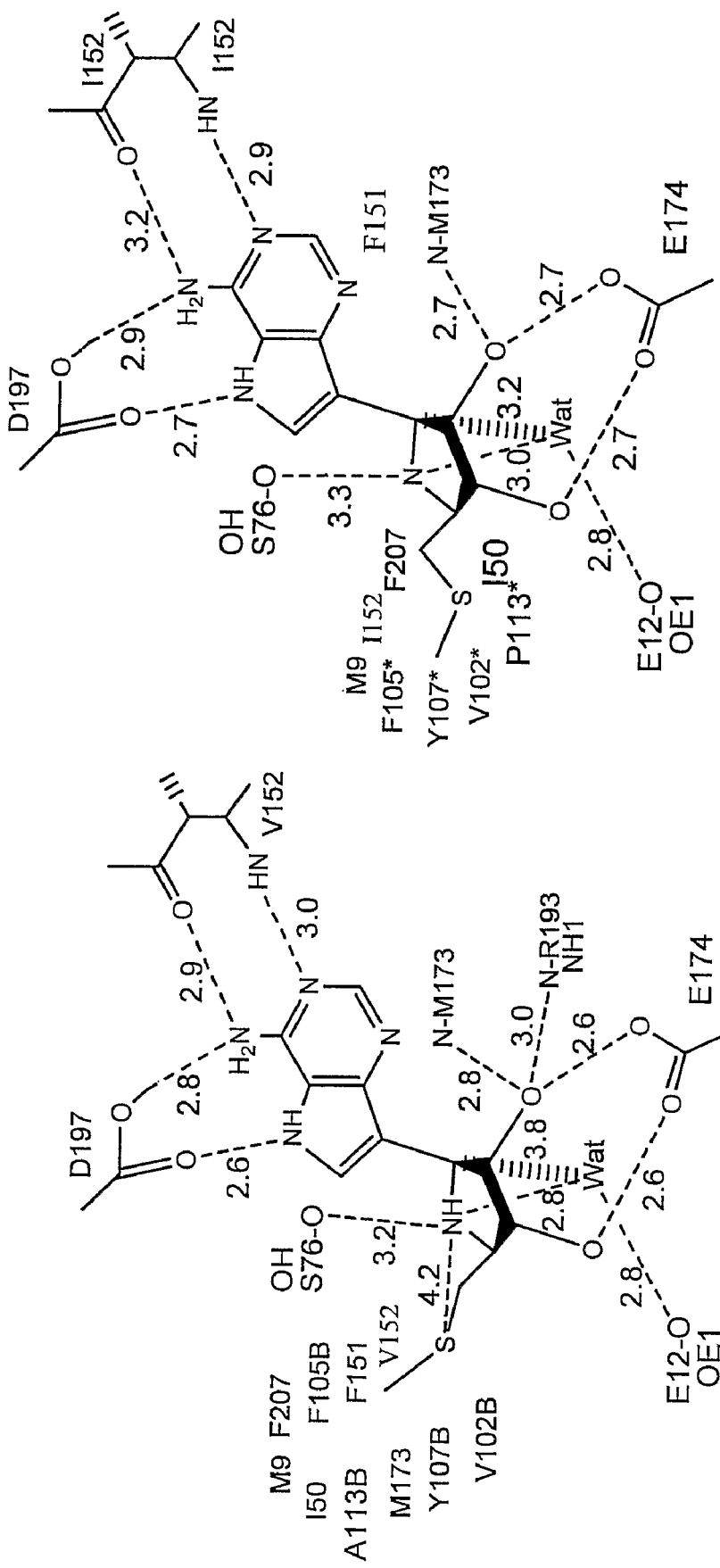
FIG. 2 shows *S. pneumoniae* MTAN and *E. coli* MTAN catalytic sites with MT-Immucillin-A.

The term "alkyl" is intended to include both straight- and branched-chain alkyl groups. The same terminology applies to the non-aromatic moiety of an aralkyl radical. Examples of alkyl groups include: methyl group, ethyl group, n-propyl group, iso-propyl group, n-butyl group, iso-butyl group, sec-butyl group, t-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group and 1-methyl-2-ethylpropyl group. The term is intended to include both saturated and unsaturated alkyl groups.

The term "aryl" means an aromatic radical having 6 to 18 carbon atoms and includes heteroaromatic radicals. Examples include monocyclic groups, as well as fused groups such as bicyclic groups and tricyclic groups. Some examples include phenyl group, indenyl group, 1-naphthyl group, 2-naphthyl group, azulenyl group, heptalenyl group, biphenyl group, indacenyl group, acenaphthyl group, fluorenyl group, phenalenyl group, phenanthrenyl group, anthracenyl group, cyclopentacyclooctenyl group, and benzocyclooctenyl group, pyridyl group, pyrrolyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, isoindolyl group, indolizinyl group, purinyl group, indazolyl group, furyl group, pyranyl group, benzofuryl group, isobenzofuryl group, thienyl group, thiazolyl group, isothiazolyl group, benzothiazolyl group, oxazolyl group, and isoxazolyl group.

The term "halogen" includes fluorine, chlorine, bromine and iodine.

The compounds are useful for the treatment of certain diseases and disorders in humans and other animals. Thus, the term "patient" as used herein includes both human and other animal patients.

The term "prodrug" as used herein means a pharmacologically acceptable derivative of the compound of formula (I), such that an in vivo biotransformation of the derivative gives the compound as defined in formula (I). Prodrugs of compounds of formula (I) may be prepared by modifying functional groups present in the compounds in such a way that the modifications are cleaved in vivo to give the parent compound.

The term "pharmaceutically acceptable salts" is intended to apply to non-toxic salts derived from inorganic or organic acids, including, for example, the following acid salts: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, p-toluenesulfonate, salicylate, succinate, sulfate, tartrate, thiocyanate, and undecanoate.

As used herein, the term "sulfonate leaving group" means an alkyl or aryl sulfonate such as methanesulfonate or benzenesulfonate, or a substituted form thereof such as bromobenzenesulfonate, trifluoromethanesulfonate or p-toluenesulfonate.

As used herein, the term "protecting group" means a group that selectively protects an organic functional group, temporarily masking the chemistry of that functional group and allowing other sites in the molecule to be manipulated without affecting the functional group. Suitable protecting groups are known to those skilled in the art and are described, for example, in *Protective Groups in Organic Synthesis* ($3^{rd}$ Ed.), T. W. Greene and P. G. M. Wuts, John Wiley & Sons Inc (1999).

Description of the Inhibitor Compounds

It is well known that substrates for enzymes, such as PNP, MTAP and MTA, are typically chiral compounds and further that only one of the enantiomeric forms interacts strongly with the enzyme.

FIG. 1 shows a contact map from the catalytic sites of human PNP and *S. pneumoniae* and *E. coli* MTANs. Based on the x-ray crystal structure of human PNP, it is known that binding of Immucillins at the catalytic sites involves favourable hydrogen bonds to both the 2' and 3' hydroxyls of the imino sugar. In the case of *E. coli* MTAN with MT-Immucillin A bound at the catalytic site, Met173 and Glu174 both form highly favourable 2.7 Angstrom bonds to the 2'-hydroxyl group and Glu174 forms a highly favourable 2.7 Angstrom bond to the 3'-hydroxyl group. In the catalytic site of *S. pneumonia* MTAN, similar hydrogen bonds are formed between the Glu174 and the 2'- and 3'-hydroxyl groups. Likewise for human PNP and complexes with DADMe-Immucillin-H, contact to the 3'-hydroxyl is known to involve a 2.9 Angstrom bond to Tyr88. Loss of these interactions in the azetidine compounds of formula (I) would be expected to cause loss of binding. However, the applicants have surprisingly found that certain of these azetidine compounds, which have no hydroxyl groups corresponding to the important 2'- and 3'-hydroxyl groups, still bind with nanomolar to picomolar affinity.

It has also previously been considered that the three-dimensional structure of the 5-membered imino sugar ring of the Immucillins is important for locating hydroxyl groups in the catalytic site in sufficient proximity to other groups to enable binding through hydrogen bond interactions. It was previously considered that 4-membered azetidine ring analogues would not meet these steric requirements necessary for inhibitory activity.

It is therefore surprising and unexpected that the azetidine compounds of the invention are inhibitors of PNP, MTAP, MTAN and/or nucleoside hydrolases. The compounds of the invention therefore represent a new class of inhibitors of PNP, MTAP, MTAN, and/or nucleoside hydrolases. As such, they are useful in treating diseases and conditions such as cancer, bacterial infections, parasitic infections, T-cell mediated diseases and other autoimmune diseases, and for immunosuppression for organ transplantation. Cancer means any type of cancer, including, but not limited to, cancers of the head, neck, bladder, bowel, skin, brain, CNS, breast, cervix, kidney, larynx, liver, oesophagus, ovaries, pancreas, prostate, lung, stomach, testes, thyroid, uterus, as well as melanoma, leukaemia, lymphoma, osteosarcoma, Hodgkin's disease, glioma, sarcoma and colorectal, endocrine, gastrointestinal cancers.

General Aspects

The compounds of the invention are useful in both free base form and in the form of salts.

It will be appreciated that the representation of a compound of formula (I), where B and/or D is a hydroxy group, is of the enol-type tautomeric form of a corresponding amide, and this will largely exist in the amide form. The use of the enol-type tautomeric representation is simply to allow fewer structural formulae to represent the compounds of the invention.

Similarly, it will be appreciated that the representation of a compound of formula (I), where B is a thiol group, is of the thioenol-type tautomeric form of a corresponding thioamide, and this will largely exist in the thioamide form. The use of the thioenol-type tautomeric representation is simply to allow fewer structural formulae to represent the compounds of the invention.

The active compounds may be administered to a patient by a variety of routes, including orally, parenterally, by inhalation spray, topically, rectally, nasally, buccally or via an implanted reservoir. The amount of compound to be administered will vary widely according to the nature of the patient and the nature and extent of the disorder to be treated. Typically the dosage for an adult human will be in the range less than 1 to 1000 milligrams, preferably 0.1 to 100 milligrams.

The specific dosage required for any particular patient will depend upon a variety of factors, including the patient's age, body weight, general health, sex, etc.

For oral administration the compounds can be formulated into solid or liquid preparations, for example tablets, capsules, powders, solutions, suspensions and dispersions. Such preparations are well known in the art as are other oral dosage regimes not listed here. In the tablet form the compounds may be tableted with conventional tablet bases such as lactose, sucrose and corn starch, together with a binder, a disintegration agent and a lubricant. The binder may be for example, corn starch or gelatin, the disintegrating agent may be potato starch or alginic acid, and the lubricant may be magnesium stearate. For oral administration in the form of capsules, diluents such as lactose and dried cornstarch may be employed. Other components such as colourings, sweeteners or flavourings may be added.

When aqueous suspensions are required for oral use, the active ingredient may be combined with carriers such as water and ethanol, and emulsifying agents, suspending agents and/or surfactants may be used. Colourings, sweeteners or flavourings may also be added.

The compounds may also be administered by injection in a physiologically acceptable diluent such as water or saline. The diluent may comprise one or more other ingredients such as ethanol, propylene glycol, an oil or a pharmaceutically acceptable surfactant.

The compounds may also be administered topically. Carriers for topical administration of the compounds of include mineral oil, liquid petrolatum, white petrolatum, propylene glycol, polyoxyethylene, polyoxypropylene compound, emulsifying wax and water. The compounds may be present as ingredients in lotions or creams, for topical administration to skin or mucous membranes. Such creams may contain the active compounds suspended or dissolved in one or more pharmaceutically acceptable carriers. Suitable carriers include mineral oil, sorbitan monostearate, polysorbate 60, cetyl ester wax, cetearyl alcohol, 2-octyldodecanol, benzyl alcohol and water.

The compounds may further be administered by means of sustained release systems. For example, they may be incorporated into a slowly dissolving tablet or capsule.

Synthesis of the Inhibitor Compounds

These compounds may be prepared by using standard methods to synthesize appropriate azetidines followed by coupling via linkers to the desired purine or 9-deazapurine. Schemes 1-5 in the Examples show indicative and non-limiting methods for preparation.

EXAMPLES

The following examples further illustrate the invention. It is to be appreciated that the invention is not limited to the examples.

General

All reagents were used as supplied; anhydrous solvents were obtained commercially. Air sensitive reactions were carried out under argon unless otherwise stated. Organic solutions were dried over $MgSO_4$ and the solvents were evaporated under reduced pressure. Chromatography solvents were distilled prior to use. Thin layer chromatography (t.l.c.) was performed on glass or aluminium sheets coated with 60 $F_{254}$ silica. Organic compounds were visualised under uv light or by use of a spray or dip of cerium(IV) sulfate (0.2%, w/v) and ammonium molybdate (5%) in sulfuric acid (2M), one of $I_2$ instrument Microanalyses were carried out by the Campbell Microanalytical Laboratory, University of Otago.

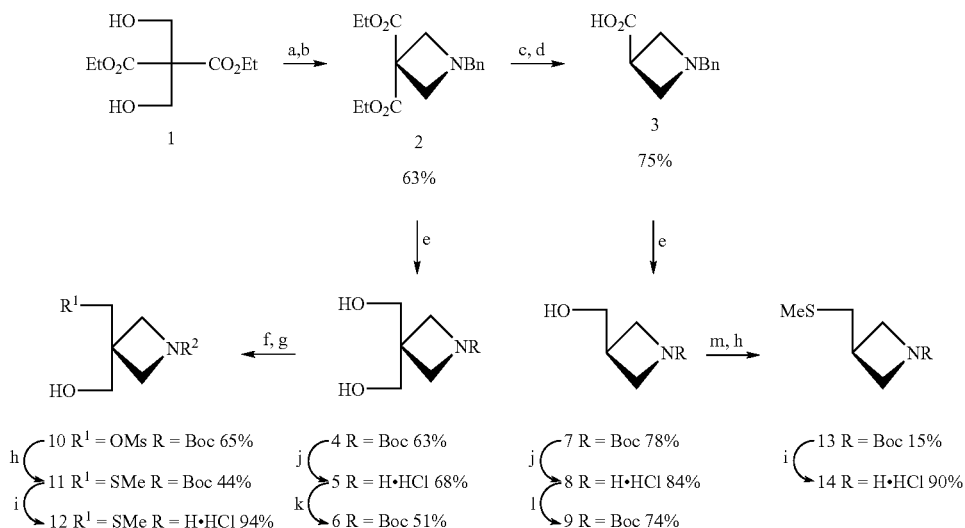

Scheme 1

Reagents: (a) Tf$_2$O, Hunigs base, acetonitrile -10° C. → -20° C.. (b) Benzylamine, Hunigs base, acetonitrile, -10° C. → 70° C.. (c) NaOH, MeOH, 50° C.. (d) Water, reflux. (e) LAH, THF, room temp. (f) Dibutyltin oxide, toluene, reflux. (g) MsCl, toluene, room temp. (h) NaSMe, DMF, room temp. (i) HCl, MeOH, room temp. (j) Pd/C, H$_2$(g), MeOH, room temp. (k) Boc$_2$O, Et$_3$N, MeOH, room temp. (l) BoC$_2$, Et$_3$N, MeOH, room temp. (m) MsCl, Hunigs base, CH$_2$Cl$_2$.

(0.2%) and KI (7%) in $H_2SO_4$ (M) or, for nitrogen-containing compounds, p-(N,N-dimethylamino)benzaldehyde (1%) in HCl (37%)-MeOH, 1:3 (100 ml) (Erlich reagent). Flash column chromatography was performed on Sorbsil C60 40/60 silica, Scharlau or Merck silica gel 60 (40-60 μm). Melting points were recorded on a Reichert hot stage microscope and are uncorrected. Optical rotations were recorded on a Perkin-Elmer 241 polarimeter with a path length of 1 dm and are in units of $10^{-1}$ deg cm$^2$ g$^{-1}$; concentrations are in g/100 ml.

NMR spectra were recorded on a Bruker AC300E spectrometer. $^1$H spectra at 300 MHz were measured in CDCl$_3$, CD$_3$OD or CD$_3$CN (internal reference Me$_4$Si, δ 0), and $^{13}$C spectra at 75.5 or 100.6 MHz in CDCl$_3$ (reference, solvent centre line, δ 77.0), CD$_3$OD (reference, solvent centre line δ 49.0) or CD$_3$CN (reference, solvent centre line δ 118.7, CN). Assignments of $^1$H and $^{13}$C resonances were based on 2D ($^1$H-$^1$H DQF-COSY, $^1$H-$^{13}$C HSQC) spectra, and DEPT experiments gave unambiguous data on the numbers of protons bonded to each carbon atom. The assignments of the $^{13}$C resonances were consistent with the multiplicities observed. Coupling constants (J) are quoted in Hz. Infrared spectra were recorded on a Perkin-Elmer 1750 IR Fourier Transform using thin films on NaCl plates (thin film). Only characteristic absorptions are quoted. High resolution mass spectra (HRMS), ES data were collected on a Waters 2790-Micromass LCT mass spectrometer operated at a resolution of 5000 full width half height. Positive ion electrospray ionisation (ES+) spectra were calibrated relative to PEG with tetraoctylammonium bromide as the internal lock mass. Negative ion ES spectra were calibrated relative to poly-DL-alanine with Leu-enkephalin as the internal lock mass. Positive ion fast atom bombardment (FAB+) HRMS were measured on a VG 7070 instrument in a glycerol matrix, and positive ion electron impact (EI+) HRMS were measured on a VG 70SE 1-Benzylazetidine-3,3-dimethanol (4). LiAlH$_4$ (1.0 M in THF, 65 mL, 65 mmol) was added dropwise to a solution of diethyl 1-benzylazetidine-3,3-dicarboxylate (1.0 g, 3.43 mmol) in THF (20 mL). The resulting suspension was stirred overnight at room temperature, quenched with water (0.25 mL), 15% aq. NaOH (0.25 mL), and water (0.75 mL), filtered through celite, and concentrated in vacuo. Chromatography (7N NH$_3$ in MeOH/CH$_2$Cl$_2$=5:95→10:90) of the resulting residue afforded 4 (450 mg, 63%) as an oil. $^1$H NMR (CDCl$_3$): δ 7.33-7.20 (m, 5H), 3.74 (s, 4H), 3.65 (s, 2H), 3.12 (s, 4H). $^{13}$C NMR (CDCl$_3$): δ 137.4, 129.02, 128.8, 127.7, 66.8, 63.3, 58.7, 41.0. HRMS for C$_{12}$H$_{17}$NO$_2$ [M$^+$] calcd, 207.1259; found, 207.1259.

Azetidine-3,3-dimethanol hydrochloride (5). Pd(OH)$_2$ (20% on C, 150 mg, 1.9 mmol) was added to a solution of 4 (400 mg, 1.9 mmol) in MeOH (4 mL) and left to stir under an atmosphere of hydrogen overnight at room temperature. The reaction was filtered through Celite® and concentrated in vacuo. Chromatography (1,4-dioxane/NH$_4$OH=50:50) of the resulting residue afforded 5 as a colourless oil which was converted to its HCl salt (200 mg, 68%) for characterisation. $^1$H NMR (D$_2$O): δ 3.97 (s, 4H), 3.69 (s, 4H). $^{13}$C NMR (D$_2$O): δ 62.4, 49.8.

tert-Butyl 3,3-bis(hydroxymethyl)azetidine-1-carboxylate (6). Di-tert-butyl dicarbonate (2.9 g, 16.40 mmol) was added portionwise to a solution of 5 (961 mg, 8.2 mmol) in MeOH (20 mL) at room temperature. After 1 h, the reaction was concentrated in vacuo. Chromatography (MeOH/CH$_2$Cl$_2$=5:95→10:90) of the resulting residue afforded 6 (900 mg, 51%) as a syrup. $^1$H NMR (CDCl$_3$): δ 3.81 (s, 4H), 3.67 (s, 4H), 1.43 (s, 9H). $^{13}$C NMR (CDCl$_3$): δ 157.2, 80.3, 66.2, 54.1, 39.8, 28.8. HRMS for C$_{10}$H$_{19}$NO$_4$ [MH$^+$] calcd, 218.1392; found, 218.1391.

1-Benzylazetidine-3-methanol (7). LiAlH$_4$ (2.3 M in THF, 10 mL, 23 mmol) was added dropwise to a suspension of 3 (obtained by saponification and decarboxylation of 2) (2.2 g, 11.50 mmol) in THF (30 mL) at room temperature and the resulting reaction was left to stir for 16 h. The reaction was quenched with water (0.7 mL), 15% aq. NaOH (0.7 mL), and water (2.1 mL), stirred for 30 min., filtered through Celite® and concentrated in vacuo. Chromatography (7N NH$_3$ in MeOH/CH$_2$Cl$_2$=5:95→10:90) of the resulting residue afforded 7 (1.6 g, 78%). $^1$H NMR (CDCl$_3$): δ 7.30-7.17 (m, 5H), 3.63 (d, J=6.2 Hz, 2H), 3.55 (s, 2H), 3.31 (t, J=7.7 Hz, 2H), 3.00 (t, J=6.1 Hz, 2H), 2.56 (m, 1H). $^{13}$C NMR (CDCl$_3$): δ 138.2, 128.9, 128.7, 127.5, 64.6, 63.9, 57.3, 33.1. HRMS for C$_{11}$H$_{15}$NO [M$^+$] calcd, 177.1154; found, 177.1150.

Azetidine-3-methanol hydrochloride (8). Pd(OH)$_2$ (20% on C, 600 mg, 7.90 mmol) was added portionwise to a stirred suspension of 7 (1.4 g, 7.90 mmol) in MeOH (20 mL, 494 mmol) under an atmosphere of hydrogen. After 24 h, the reaction was filtered through Celite® and concentrated in vacuo. The resulting residue was converted to the HCl salt to afford 8 (820 mg, 84%) as a syrup which was characterised without additional purification. $^1$H NMR (D$_2$O): δ 4.20 (t, J=9.8 Hz, 2H), 3.98 (m, 2H), 3.75 (d, J=5.4, 2H), 3.11 (m, 1H). $^{13}$C NMR (D$_2$O): δ 61.7, 48.8, 48.8, 33.6. HRMS for C$_4$H$_9$NO [M$^+$] calcd, 87.0684; found, 87.0683.

tert-Butyl 3-(hydroxymethyl)azetidine-1-carboxylate (9). Et$_3$N (1 mL, 7.1 mmol) was added dropwise to a stirred solution of 8 (500 mg, 4.0 mmol) in MeOH (5 mL). After 5 min, di-tert-butyl dicarbonate (846 mg, 5.0 mmol) was added and the reaction stirred for 16 h and then concentrated in vacuo. Chromatography (MeOH/CH$_2$Cl$_2$=5:95→10:80) of the resulting residue afforded 9 as a colourless oil (560 mg, 74%). $^1$H NMR (CDCl$_3$): δ 3.97 (t, J=8.5 Hz, 2H), 3.71 (m, 4H), 2.69 (m, 1H), 1.43 (s, 9H). $^{13}$C NMR (CDCl$_3$): δ 156.9, 79.8, 64.5, 51.7, 30.9, 28.7. HRMS for C$_{13}$H$_{17}$NO$_3$ [M$^+$] calcd, 187.1208; found, 187.1207.

tert-Butyl 3-[(hydroxymethyl)-34(methanesulfonyloxy) methyl]azetidine-1-carboxylate (10). Dibutyltin oxide (1.24 g, 5.0 mmol) was added to a stirred suspension of 6 (900 mg, 4.1 mmol) in toluene (10 mL) and heated to reflux for 1 h. The reaction was cooled to room temperature and then methanesulfonyl chloride (0.39 mL, 5.0 mmol) was added dropwise to the clear solution and the resulting reaction allowed to stand for 16 h. Chromatography (MeOH/CH$_2$Cl$_2$=5:95) of the crude solution afforded 10 as an oil (800 mg, 2709 μmol, 65%). $^1$H NMR (CDCl$_3$): δ 4.40 (s, 2H), 3.78 (s, 2H), 3.73 (s, 4H), 3.07 (s, 3H), 1.44 (s, 9H). $^{13}$C NMR (CDCl$_3$): δ 156.8, 80.4, 70.5, 63.6, 53.6, 38.9, 37.6, 28.7. HRMS for C$_{11}$H$_{21}$NO$_6$S [MH$^+$] calcd, 207.1259; found, 207.1259.

tert-Butyl 3-(hydroxymethyl)-3-[(methanesulfonyloxy) methyl]azetidine-1-carboxylate (11). Sodium thiomethoxide (285 mg, 4.1 mmol) was added portionwise to a stirred solution of 10 (800 mg, 2.7 mmol) in DMF (5 mL) at room temperature. After 3 h, the reaction was diluted with toluene (100 mL), washed with water (25 mL) and brine (25 mL), dried (MgSO$_4$) and concentrated in vacuo. Chromatography (MeOH/CH$_2$Cl$_2$=5:95) of the crude residue afforded 11 as an oil (450 mg, 67%). $^1$H NMR (CDCl$_3$): δ 3.75 (s, 2H), 3.74 (d, J=8.8 Hz, 2H), 3.66 (d, J=8.8 Hz, 2H), 2.87 (s, 2H), 2.16 (s, 3H), 1.44 (s, 9H). $^{13}$C NMR (CDCl$_3$): δ 156.9, 80.0, 65.8, 56.1, 40.1, 39.9, 28.7, 17.5. HRMS for C$_{11}$H$_{21}$NO$_3$S [MH$^+$] calcd, 247.1242; found, 247.1246.

3-(Methylthiomethyl)azetidin-3-methanol hydrochloride (12). HCl (30% aq., 1.5 mL, 49 mmol) was added dropwise to a solution of 11 (430 mg, 17 mmol) in MeOH (4.5 mL). The resulting solution was left at room temperature for 1 h and concentrated in vacuo to afford 12 as a syrup (300 mg, 94%) which was used in the next step without purification or characterisation.

tert-Butyl 3-(methylthiomethyl)azetidine-1-carboxylate (13). Methanesulfonyl chloride (0.53 mL, 6.8 mmol) was added dropwise to a stirred solution of 9 (530 mg, 2.8 mmol) and Hunig's base (0.986 mL, 5.6 mmol) in CH$_2$Cl$_2$ (10 mL) and left overnight at room temperature. The reaction was then diluted with CH$_2$Cl$_2$ (100 mL) and washed with water (25 mL), brine (25 mL), dried (MgSO$_4$) and concentrated in vacuo. Sodium thiomethoxide (218 mg, 3109 μmol) was added portionwise to a solution of the residue, presumably tert-butyl 3-(methanesulfonyloxymethyl)azetidine-1-carboxylate (550 mg, 73%), in DMF (5 mL) and stirred at room temperature overnight. The reaction was diluted with toluene (100 mL) and washed with water (25 mL), brine (25 mL), dried (MgSO$_4$) and concentrated in vacuo. Chromatography (MeOH/CH$_2$Cl$_2$=5:95) of the resulting residue afforded 13 as an oil (120 mg, 27%). $^1$H NMR (CDCl$_3$): δ 3.98 (m, 2H), 3.54 (m, 2H), 2.65 (brs, 3H), 2.03 (s, 3H), 1.37 (s, 9H). $^{13}$C NMR (CDCl$_3$): δ 155.3, 78.3, 53.1, 37.4, 27.4, 14.5.

3-(Methylthiomethyl)azetidine hydrochloride (14). HCl (30% aq., 1.5 mL, 49 mmol) was added dropwise to a solution of 13 (120 mg, 0.55 mmol) in MeOH (4.5 mL). The resulting solution was left at room temperature for 1 h and concentrated in vacuo to afford 14 (76 mg, 90%) as a syrup which was used in the next step without purification or characterisation.

Scheme 2

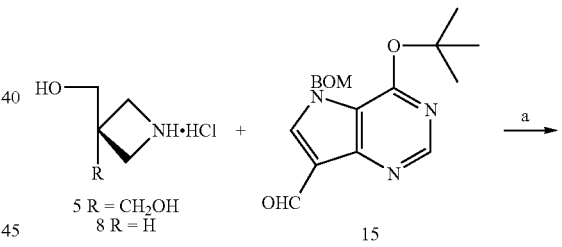

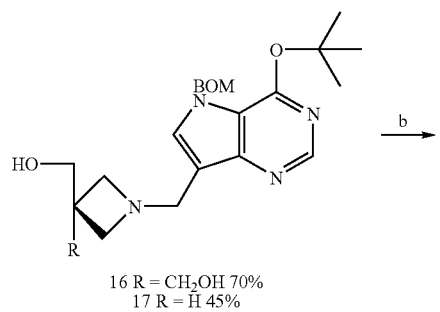

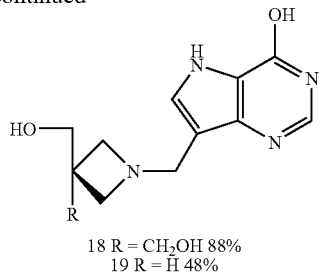

18 R = CH$_2$OH 88%
19 R = H 48%

Reagents: (a) NaCNBH$_3$, MeOH, room temp. (b) HCl, MeOH, reflux.

1-[(7-Benzyloxymethyl-4-tert-butoxy-9-deazapurin-9-yl)methyl]azetidine-3,3-dimethanol (16). 7-Benzyloxymethyl-6-tert-butoxy-9-deazapurine-9-carbaldehyde (15) (219 mg, 645 μmol) was added to a suspension of 5.HCl (90 mg, 586 μmol) in methanol (5 mL) and the resulting suspension stirred for 5 min. NaBH$_3$CN (55.2 mg, 879 μmol) was then added and the resulting reaction stirred overnight at room temperature. The crude reaction was absorbed onto silica and concentrated in vacuo. Chromatography (MeOH/CH$_2$Cl$_2$=10:90→20:80) of the resulting residue afforded 16 as a syrup (180 mg, 70%). $^1$H NMR (CDCl$_3$) 8.42 (s, 1H), 7.81 (s, 1H), 7.23-7.14 (m, 5H), 5.74 (s, 2H), 4.54 (brs, 2H), 4.51 (s, 2H), 4.16 (brs, 4H), 3.67 (brs, 4H), 1.66 (s, 9H). $^{13}$C NMR (CDCl$_3$) 156.8, 150.8, 149.4, 137.5, 135.8, 128.7, 128.1, 127.8, 117.2, 104.6, 84.3, 78.1, 70.0, 62.4, 57.2, 48.5, 42.5, 28.9. HRMS for C$_{24}$H$_{32}$N$_4$O$_4$ [MH$^+$] calcd, 441.2502; found, 441.2509.

1-[(9-Deazahypoxanthin-9-yl)methyl]azetidine-3,3-dimethanol (18). Conc. HCl (1.5 mL, 49 mmol) was added to a solution of 16 (98 mg, 222 μmol) in MeOH (1.5 mL) and the resulting solution heated at reflux for 2.5 h. The reaction was cooled to room temperature and concentrated in vacuo. Chromatography (CH$_2$Cl$_2$/MeOH/NH$_4$OH=50:40:10) afforded 18 as a syrup (52 mg, 88% yield) which was converted to the HCl salt for characterisation. $^1$H NMR (D$_2$O): δ 8.00 (s, 1H), 7.70 (s, 1H), 4.41 (s, 2H), 4.04 (q, J=10.9 Hz, 4H), 3.68 (s, 2H), 3.50 (s, 2H). $^{13}$C NMR (D$_2$O): δ 155.3, 114.3, 143.4, 131.7, 118.1, 105.02, 62.3, 61.6, 55.8, 47.4, 41.3. HRMS for C$_{12}$H$_{18}$N$_4$O$_3$ [MH$^+$] calcd, 265.1301; found, 265.1308. Anal. (C$_{12}$H$_{16}$N$_4$O$_3$.3HCl) C, H, N.

1-[(7-Benzyloxymethyl-6-tert-butoxy-9-deazapurin-9-yl)methyl]azetidine-3-methanol (17). 7-Benzyloxymethyl-6-tert-butoxy-9-deazapurine-9-carbaldehyde (15) (272 mg, 0.80 mmol) was added to a stirred suspension of 8 (90 mg, 0.73 mmol) in MeOH (5 mL) and stirred for 5 min. NaBH$_3$CN (68.6 mg, 1.1 mmol) was then added and the resulting reaction stirred overnight at room temperature. The crude reaction was absorbed onto silica and concentrated in vacuo. Chromatography (MeOH/CH$_2$Cl$_2$=5:95→20:80) of the resulting residue afforded 17 as a syrup (135 mg, 45%). $^1$H NMR (CDCl$_3$): δ 8.35 (s, 1H), 7.72 (s, 1H), 7.20-7.08 (m, 5H), 5.68 (s, 2H), 4.44 (s, 2H), 4.43 (s, 2H), 4.17 (t, J=10.0 Hz, 2H), 4.06 (t, J=6.3 Hz, 2H), 3.64 (d, J=2.9 Hz, 2H), 2.90 (m, 1H), 1.60 (s, 9H). $^{13}$C NMR (CDCl$_3$): δ 156.7, 150.9, 149.7, 137.4, 135.5, 128.8, 128.1, 127.8, 117.2, 104.8, 84.2, 78.1, 70.8, 60.4, 55.4, 48.2, 31.4, 28.9. HRMS for C$_{23}$H$_{30}$N$_4$O$_3$ [MH$^+$] calcd, 411.2396; found, 411.2409.

1-[(9-Deazahypoxanthin-9-yl)methyl]azetindine-3-methanol (19). Compound 17 (95 mg, 231 μmol) was dissolved in conc. HCl (5 mL, 1.63 mmol) and heated at reflux for 2 h and the reaction was then concentrated in vacuo. Chromatography (CH$_2$Cl$_2$/MeOH/NH$_4$OH=5:4:1) of the resulting residue afforded 19 as a white solid (28 mg, 48%). $^1$H NMR (D$_2$O) δ 7.82 (1H, s), 7.28 (2H, s), 4.70 (1H, s), 3.71 (2H, s), 3.54 (d, J=6.3 Hz, 2H), 3.48 (t, J=8.5 Hz, 2H), 3.17 (t, J=7.8 Hz, 2H), 2.61 (septet, J=7.1 Hz, 1H). $^{13}$C NMR (D$_2$O) δ 157.4, 144.7, 144.06, 129.1, 117.8, 109.52, 63.2, 55.3, 55.3, 49.6, 31.3. HRMS for C$_{11}$H$_{16}$N$_4$O$_3$ [MH$^+$] calcd, 235.1196; found, 235.1194. Anal. (C$_{11}$H$_{16}$N$_4$O$_3$) C, H, N.

Scheme 3

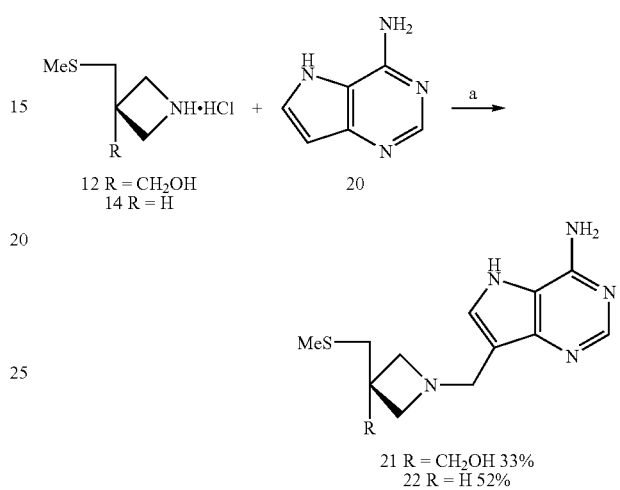

21 R = CH$_2$OH 33%
22 R = H 52%

Reagents: (a) HCHO, NaOAc, 1,4-Dioxane, H$_2$O, 95° C.

1-[(9-Deazaadenin-9-yl)methyl]-3-methylthiomethylazetidine-3-methanol hydrochloride (21). NaOAc (134 mg, 1633 μmol) was added to a solution of 12.HCl (300 mg, 1.6 mmol) in water (4 mL) and 1,4-dioxane (2 mL) and the resulting suspension stirred at room temperature for 5 min. Formaldehyde solution (0.131 mL, 1.6 mmol) was then added dropwise followed by 9-deazaadenine (20) (241 mg, 1.8 mmol) and the resulting suspension heated to 95° C. (bath temp). After 2 h the crude reaction was absorbed onto silica and concentrated in vacuo. Chromatography (NH$_4$OH/MeOH/CH$_2$Cl$_2$=2:48:50) of the resulting residue afforded 21 as a syrup (180 mg, 33.4%). $^1$H NMR (D$_2$O) δ 7.88 (brs, 1H), 7.29 (brs, 1H), 3.81 (s, 2H), 3.46 (s, 2H), 3.37 (dd, J=17.5, 9.8 Hz, 4H), 2.46 (s, 2H), 2.55 (m, 2H), 1.83 (s, 3H). $^{13}$C NMR (D$_2$O) δ 150.5, 150.2, 145.2, 130.5, 113.8, 106.2, 64.2, 57.8, 48.3, 39.8, 38.6, 16.5. HRMS for C$_{13}$H$_{19}$N$_5$OS [MH$^+$] calcd, 294.1388; found, 294.1388. Anal. (C$_{13}$H$_{19}$N$_5$OS) C, H, N.

1-[(9-Deazaadenin-9-yl)methyl]-3-methylthiomethylazetidine (22). NaOAc (0.048 g, 0.586 mmol) was added to a solution of 14.HCl (0.09 g, 0.586 mmol) in water (2 mL) and stirred for 15 min. Formaldehyde solution (0.047 mL, 0.586 mmol), 9-deazaadenine (20) (86 mg, 0.644 mmol) and 1,4-dioxane (1 mL) were added consecutively and the resulting suspension stirred at 95° C. for 3 h. The crude reaction was absorbed onto silica and concentrated in vacuo. Chromatography (NH$_4$OH/MeOH/CH$_2$Cl$_2$=2:48:50) of the resulting residue afforded product contaminated with ammonium acetate. Further chromatography using Amberlyst 15 (H$_2$O→2% aq. NH$_4$OH) afforded 22 as a syrup (80 mg, 52%). $^1$H NMR (D$_2$O): δ 8.06 (s, 1H), 7.34 (s, 1H), 3.71 (s, 2H), 3.40 (m, 2H), 2.95 (m, 2H), 2.55 (m, 3H), 1.93 (s, 3H). $^{13}$C NMR (D$_2$O): δ 152.5, 151.4, 147.2, 129.8, 115.6, 112.4, 60.2, 60.2, 52.4, 39.1, 31.7, 15.7. HRMS for C$_{12}$H$_{17}$N$_5$S [MH$^+$] calcd, 264.1283; found, 264.1288. Anal. (C$_{12}$H$_{17}$N$_5$S.2/3H$_2$O) C, H, N.

Scheme 4

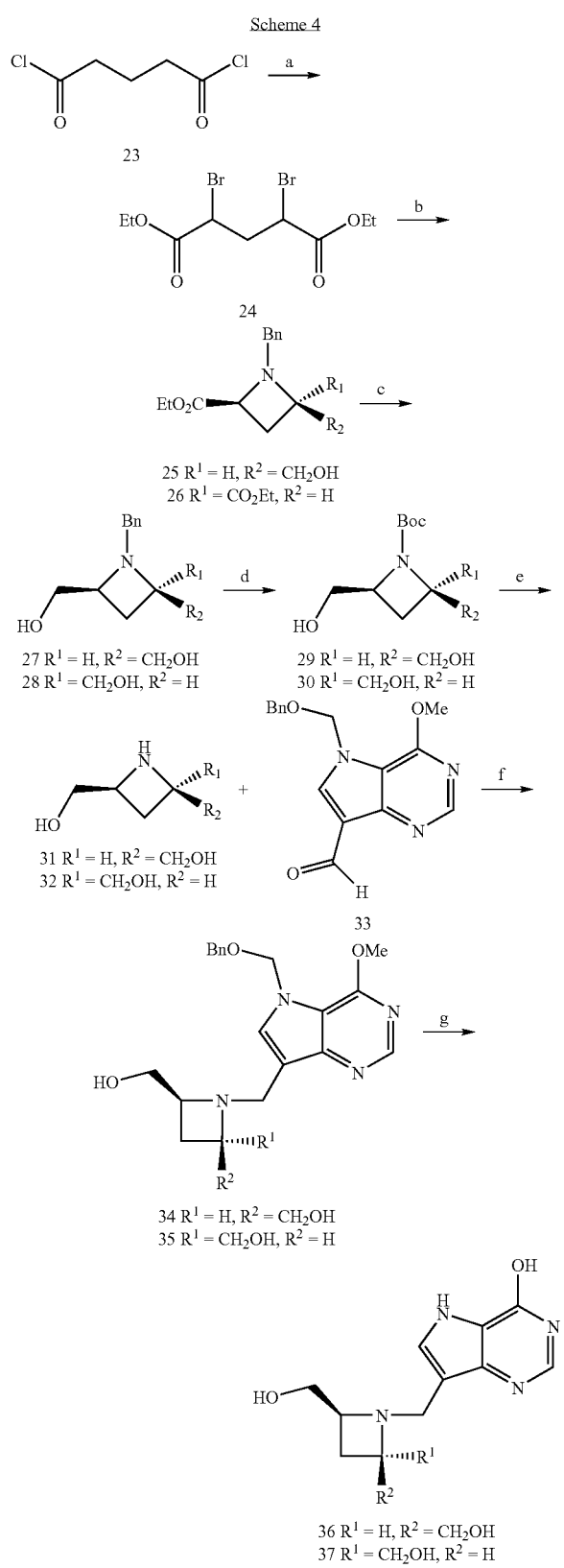

Reagents: a) i) Br₂, hv; ii) EtOH, H₂SO₄; b) BnNH₂, C₆H₈; c) LiAlH₄, Et₂O; d) H₂ Pd(OH)₂/C, Boc₂O; e) i) HCl MeOH/H₂O; f) NaBH₃CN, EtOH; g) conc. HCl, reflux.

meso-tert-Butyl 2,4-cis-2,4-bis(hydroxymethyl)azetidine-1-carboxylate (29). 2,4-cis-1-Benzyl-2,4-bis(hydroxymethyl)azetidine (27) (Guanti, G.; Riva, R. *Tetrahedron-Asymmetry* 2001, 12(4), 605-618) (1.16 g, 5.60 mmol) was dissolved in EtOH (10 mL) and di-tert-butyl dicarbonate (2.44 g, 11.2 mmol) added followed by 20% Pd(OH)₂/C (200 mg). The atmosphere was replaced with hydrogen by the successive application of vacuum and then a balloon of hydrogen was fitted to the reaction vessel. The reaction mixture was allowed to stir overnight, then the suspension was filtered through Celite®, the volatiles removed under reduced pressure and the residue purified by flash chromatography on silica (60:40 to 100:0 EtOAc/hexane) to give 29 as a colourless oil (915 mg, 75%); ¹H NMR (300 MHz, CDCl₃) δ 4.27-4.16 (m, 2H), 4.20-3.05 (br s, 2H), 3.77 (br d, J=11.4 Hz, 2H), 3.61 (br dd, J=11.4, 5.4 Hz, 2H), 2.18 (ddd, J=11.4, 8.7, 8.7 Hz, 1H), 1.98 (ddd, J=11.4 6.7, 6.7 Hz, 1H), 1.43 (s, 9H); ¹³C NMR (75 MHz, CDCl₃) δ 157.4, 80.8, 64.5, 60.3, 28.2, 19.7; ESI-HRMS for C₁₀H₁₉N₁O₄Na₁ [M+Na⁺] calcd, 240.1212; found, 240.1218; Anal. C₁₀H₁₉N₁O₄.(0.2H₂O) C, H, N.

meso-2,4-cis-2,4-Bis(hydroxymethyl)azetidine hydrochloride (31). A solution of 29 (480 mg, 2.20 mmol) in 2:1 MeOH/conc. HCl (10 mL) was stirred for 20 min and then concentrated under reduced pressure. The product was azeotropically dried by the addition and evaporation of acetonitrile several times giving 31 as a colourless hygroscopic solid after drying under high vacuum (344 mg, 100%); ¹H NMR (300 MHz, D₂O) δ 4.62-4.50 (m, 2H), 3.83 (d, J=4.8 Hz, 4H), 2.50 (dt, J=12.0, 9.0 Hz, 1H), 2:37 (dt, J=12.0, 9.0 Hz, 1H); ¹³C NMR (75 MHz, D₂O) δ 60.9, 58.2, 22.5.

(±)tert-Butyl 2,4-trans-2,4-bis(hydroxymethyl)azetidine-1-carboxylate (30). To a stirred solution of (±)N-benzyl 2,4-trans-2,4-bis(hydroxymethyl)azetidine (28) (Guanti, G.; Riva, R. *Tetrahedron-Asymmetry* 2001, 12(4), 605-618) (570 mg, 2.75 mmol) in EtOH (10 mL) was added di-tert-butyl dicarbonate (1.2 g, 5.5 mmol) and then 20% Pd(OH)₂/C (400 mg). The atmosphere was replaced with hydrogen by successive applications of vacuum and a hydrogen balloon fitted to the reaction vessel. The reaction mixture was stirred overnight and then filtered through Celite®. The mixture was concentrated under reduced pressure and the product purified by flash chromatography on silica (EtOAc) to give 30 as a colourless oil (490 mg, 82%); ¹H NMR (300 MHz, CDCl₃) δ 4.58-4.23 (m, 3H), 3.93-3.62 (m, 4H), 2.32 (br s, 1H), 2.15-1.85 (br m, 2H), 1.47 (s, 9H); ¹³C NMR (75 MHz, CDCl₃) δ 156.5, 81.4, 67.0, 64.8, 61.7, 61.5, 28.3, 20.8; ESI-HRMS for C₁₀H₁₉N₁O₄Na₁ [M+Na] calcd, 240.1212; found, 240.1213.

(±)2,4-trans-2,4-Bis(hydroxymethyl)azetidine hydrochloride (32). A solution of 30 (480 mg, 2.20 mmol) in 2:1 MeOH/conc. HCl (10 mL) was stirred for 20 min and then concentrated under reduced pressure. The product was azeotropically dried by the addition and evaporation of acetonitrile several times giving 32 as a colourless hygroscopic solid (339 mg, 99%); ¹H NMR (300 MHz, D₂O) δ 4.50-4.39 (m, 2H), 3.91-3.87 (m, 4H), 2.44 (t, J=8.1 Hz, 2H); ¹³C NMR (75 MHz, CDCl₃) δ 61.0, 59.0, 22.3.

meso-2,4-cis-1-[(7-Benzyloxymethyl-9-deaza-6-methoxy-purin-9-yl)methyl]azetidine-2,4-dimethanol hydrochloride (34). To a stirred solution of aldehyde 33 (277 mg, 0.93 mmol) in EtOH (3 mL) at ambient temperature was added 31.HCl (143 mg, 0.93 mmol) followed after 5 min by NaBH₃CN (88 mg, 0.48 mmol). The reaction was left to stir overnight after which time all of the starting aldehyde had dissolved. The reaction mixture was absorbed onto silica gel, the volatiles removed under reduced pressure and the product purified by flash chromatography (CHCl₃/MeOH=95:5 to 80:20) to give colourless crystals which were taken up in water, conc. HCl added then concentrated under reduced pressure to dryness to afford 34 (70 mg, 54%); ¹H NMR (300

MHz, D$_2$O) δ 8.61 (s, 1H), 8.02 (s, 1H), 7.25-7.07 (m, 5H), 5.90 (s, 2H), 4.68 (s, 2H), 4.58 (s, 2H), 4.54-4.43 (m, 2H), 4.24 (s, 3H), 3.72 (dd, J=13.2, 5.7 Hz, 2H), 3.61 (dd, J=13.2, 3.2 Hz, 2H), 2.47 (dt, J=12.1, 9.0 Hz, 1H), 2.28 (dt, J=9.6, 9.0 Hz, 1H); $^{13}$C NMR (75 MHz, D$_2$O) δ 159.4, 148.4, 142.5, 139.9, 137.0, 128.8, 128.6, 128.2, 116.7, 102.6, 78.7, 72.0, 66.6, 60.2, 56.5, 47.3, 20.4; ESI-HRMS for C$_{21}$H$_{27}$N$_4$O$_4$[M+H$^+$] calcd, 399.2032; found, 399.2046.

meso-[(9-Deazahypoxanthin-9-yl)methyl]azetidine-2,4-dimethanol hydrochloride (36). A solution of 34 (114 mg, 0.26 mmol) in conc. HCl (3 mL) was heated under reflux for 3 h and then cooled to room temperature. The mixture was evaporated to dryness under reduced pressure and residual HCl removed by the addition and evaporation of acetonitrile several times. The residue was absorbed onto silica and purified by flash chromatography (2-propanol/H$_2$O/NH$_4$OH=9:1:1) to give a colourless gum. This was converted to its hydrochloride salt for characterization by the addition and evaporation of conc. HCl yielding 36 as a colourless solid (53 mg, 67%) after trituration with 2-propanol; HPLC purity 99.5% (220 nm); $^1$H NMR (300 MHz, D$_2$O) δ 8.21-8.15 (m, 1H), 7.75-7.72 (m, 1H), 4.57 (s, 2H), 4.50 (dddd, J=9.0, 9.0, 5.5, 3.6 Hz, 2H), 3.69 (13.3, 5.5 Hz, 2H), 3.58 (dd, J=13.3, 3.6 Hz, 2H), 2.48-2.36 (m, 1H), 2.28 (dt, J=12.1, 9.0, Hz, 1H); $^{13}$C NMR (75 MHz, D$_2$O, freebase) δ 155.9, 144.2, 142.9, 130.2, 117.5, 111.5, 64.5, 62.7, 49.1, 24.0; ESI-HRMS for C$_{12}$H$_{17}$N$_4$O$_3$ [M+H$^+$] calcd, 265.1301; found, 265.1316; Anal. C$_{12}$H$_{16}$N$_4$O$_3$.(2.6H$_2$O)C, H, N.

(±)2,4-trans-1-[(7-Benzyloxymethyl-9-deaza-6-methoxypurin-9-yl)methyl]azetidine-2,4-dimethanol hydrochloride (35). To a stirred solution of aldehyde 33 (210 mg, 0.70 mmol) in EtOH (7 mL) at ambient temperature was added 32.HCl (100 mg, 0.65 mmol) followed after 5 min by NaBH$_3$CN (67 mg, 1.0 mmol). The reaction was left to stir overnight after which time most of the starting aldehyde had dissolved. The reaction mixture was absorbed onto silica gel under reduced pressure and the product purified by flash chromatography (CHCl$_3$/MeOH=95:5 to 80:20) to give colourless crystals which were taken up in water, conc. HCl added then the mixture concentrated under reduced pressure to afford 35 as a colourless hygroscopic solid (235 mg, 83%); $^1$H NMR (300 MHz, D$_2$O) δ 8.78 (s, 1H), 8.13 (s, 1H), 7.20-7.04 (m, 5H), 5.86 (s, 2H), 4.62 (s, 2H), 4.62-4.47 (m, 3H), 4.27 (s, 3H), 4.26-4.04 (m, 2H), 3.57 (br d, J=10.5 Hz, 1H), 3.30 (br d, J=10.5 Hz, 1H), 2.46 (t, J=8.1 Hz, 2H); $^{13}$C NMR (75 MHz, D$_2$O) δ 160.0, 147.4, 140.2, 140.1, 136.9, 128.9, 128.7, 128.3, 116.8, 102.3, 78.8, 72.1, 68.4, 65.0, 60.2, 58.8, 57.0, 42.2, 20.8; ESI-HRMS for C$_{21}$H$_{27}$N$_4$O$_4$ [M+H$^+$] calcd, 399.2032; found, 399.2014.

(±)2,4-trans-[(9-Deazahypoxanthin-9-yl)methyl]azetidine-2,4-dimethanol hydrochloride (37). A solution of azetidine 35 (60 mg, 0.13 mmol) was heated to reflux in conc. HCl (5 mL). After 3 h the mixture was concentrated under reduced pressure and the residue purified by successive flash chromatography on silica (9:1:1 2-propanol/H$_2$O/NH$_4$OH then 65:35:7:1 CHCl$_3$/MeOH/H$_2$O/NH$_4$OH). The isolated product was dissolved in 1 M HCl (2 mL) and again concentrated in vacuo to give 37 as a hygroscopic colourless gum (35 mg, 84%); HPLC purity 96% (290 nm); $^1$H NMR (300 MHz, D$_2$O) δ 8.57 (s, 1H), 7.72 (s, 1H), 4.65 (d, J=6.9 Hz, 2H), 4.60-4.48 (m, 2H), 4.21 (dd, J=14.2, 6.4 Hz, 1H), 14.2, 3.0 Hz, 1H), 3.52 (dd, J=13.2, 4.6 Hz, 1H), 3.22 (dd, J=13.2, 3.4 Hz, 1H), 2.54-2.37 (m, 2H); $^{13}$C NMR (75 MHz, D$_2$O) δ 154.2, 144.7, 137.7, 132.4, 118.6, 104.1, 67.8, 64.7, 60.0, 58.8, 42.5, 20.6; ESI-HRMS for C$_{12}$H$_{17}$N$_4$O$_3$[M+H$^+$] calcd, 265.1301; found, 265.1316.

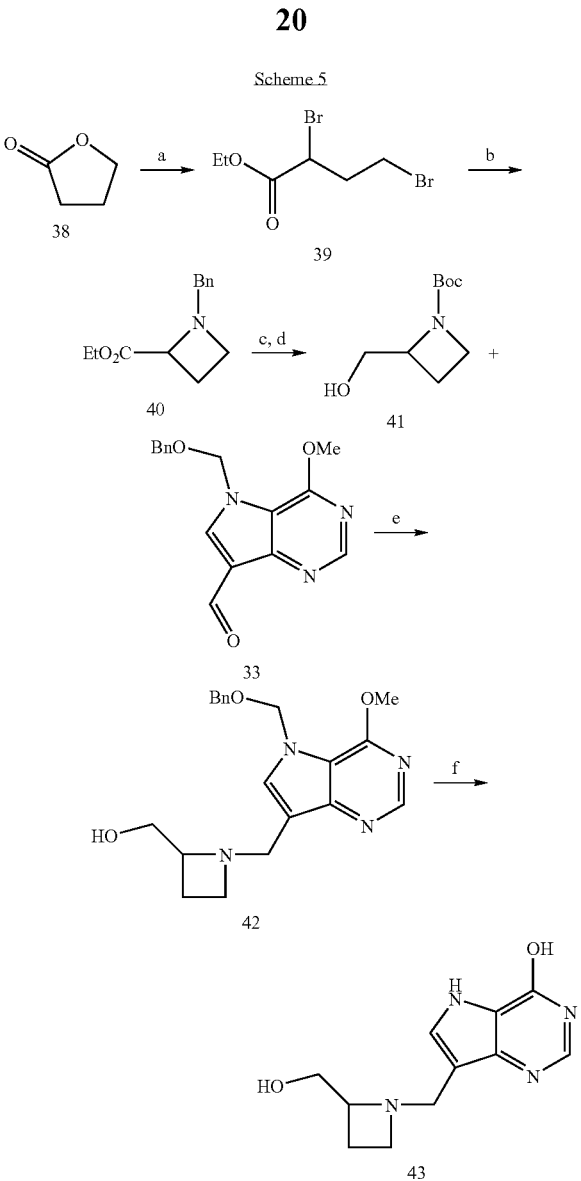

Scheme 5

Reagents: a) Br$_2$, PBr$_3$; b) BnNH$_2$, NEt$_3$, CH$_3$CN; c) LiAlH$_4$, Et$_2$O; d) H$_2$, Pd(OH)$_2$/C, Boc$_2$O; e) i) HCl MeOH/H$_2$O; ii) NaBH$_3$CN, EtOH; f) conc. HCl, reflux.

Ethyl 2,4-dibromobutanoate (39). (Wasserman, H. H. et al. J Org. Chem. 1981, 46(15), 2991-2999). To a mixture of γ-butyrolactone (38) (22.4 g, 0.26 mol) and phosphorus tribromide (0.5 g, 1.8 mmol) heated to 110° C. was slowly added bromine (41.6 g, 0.26 mol) over 30 minutes. The reaction progress was monitored by the disappearance of bromine colour from the reaction mixture. The reaction was kept at this temperature for another 15 minutes then cooled in ice and ethanol (100 ml) carefully added. The reaction mixture was then acidified with sulfuric acid (1 ml) and heated to reflux for 2 hours and then cooled to room temperature and neutralized with solid NaHCO$_3$ until no more CO$_2$ was evolved. The mixture was concentrated under reduced pressure and then diluted with water and CH$_2$Cl$_2$. The layers separated and then aqueous layer extracted with CH$_2$Cl$_2$. The combined organic layers were dried and then concentrated under reduced pressure giving a pale brown oil which was distilled to give 39 as a colourless oil (40.9 g, 57%); bp 62° C., 0.3 mmHg; $^1$H NMR (300 MHz, CDCl$_3$) δ 4.49 (dd, J=7.9, 6.2 Hz, 1H), 4.30-4.20 (m, 2H), 3.54 (t, J=6.2 Hz, 2H), 2.56-2.46 (m, 2H), 1.31 (t, J=6.9 Hz, 3H).

(±)Ethyl 1-benzylazetidine-2-carboxylate (40). (Wasserman, H. H. et al. *J Org. Chem.* 1981, 46(15), 2991-2999). A mixture of (±)ethyl 2,4-dibromobutanoate (39) (15 g, 54.8 mmol), triethylamine (16.6 g, 164 mmol) and benzylamine (5.87 g, 54.8 mmol) was heated to reflux for 3 hours then concentrated under reduced pressure to give a solid suspension. Water (150 ml) was then added and the mixture extracted with ether (2×100 ml). The organic phase was dried and then concentrated under reduced pressure and the residue purified by dry flash chromatography on silica (hexanes then 1:3 ethyl acetate/hexanes) to give 40 as a pale yellow oil (6.3 g, 53%); $^1$H NMR (300 MHz, CDCl$_3$) δ 7.37-7.27 (m, 5H), 4.16-4.03 (m, 2H), 3.82 (d, J=12.6 Hz, 1H), 3.73 (dd, J=8.4, 8.4 Hz, 1H), 3.61 (d, J=12.8 Hz, 1H), 3.34 (ddd, J=7.4, 7.4, 2.0 Hz, 1H), 2.95 (ddd, J=7.4, 7.4, 7.4 Hz, 1H), 2.44-2.31 (m, 1H), 2.27-2.16 (m, 1H), 1.20 (t, J=7.2 Hz, 3H); $^{13}$C NMR (75 MHz, CDCl$_3$) δ 172.5, 137.1, 129.0, 128.7, 128.2, 127.1, 64.5, 62.4, 60.5, 50.8, 21.5, 14.0.

(±)tert-Butyl 2-hydroxymethylazetidine-1-carboxylate (41). (Abreo, M. A. et al. *J Med Chem.* 1996, 39(4), 817-825). To a stirred solution of (±)ethyl 1-benzylazetidine-2-carboxylate (40) (3.67 g, 16.7 mmol) in dry diethyl ether (50 ml) cooled to 4° C. was slowly added a solution of lithium aluminium hydride in diethyl ether (1.0 M, 16 ml, 16.0 mmol). The reaction was allowed to stir at ambient temperature for 1 hour and then carefully quenched with ethyl acetate followed by 2M NaOH (4 ml). The reaction mixture was allowed to stir for 1 hour and then the aluminates were removed by filtration and the filtrate concentrated under reduced pressure to give a colourless oil. The oil was dissolved in ethanol (20 ml) and then di-tert-butyl dicarbonate (5.24 g, 24 mmol) and 20% Pd(OH)$_2$/C (500 mg) were added. The atmosphere was replaced by hydrogen by the successive application of vacuum and then a hydrogen balloon fitted to the reaction which was allowed to stir overnight. The hydrogen atmosphere was replaced with Ar and then the suspension filtered through Celite®. The filtrate was concentrated under reduced pressure and the residue purified by flash chromatography to give 41 as a colourless oil (850 mg, 28%); R$_f$ 0.50 (2:1 EtOAc/hexane); $^1$H NMR (300 MHz, CDCl$_3$) δ 4.52-4.38 (m, 1H), 3.94-3.63 (m, 4H), 2.25-2.12 (m, 1H), 2.02-1.87 (m, 1H), 1.46 (s, 9H).

(±)(1-((5-(Benzyloxymethyl)-4-methoxy-5H-pyrrolo[3,2-d]pyrimidin-7-yl)methyl)azetidin-2-yl)methanol (42). To a stirred solution of azetidine 41 (162 mg, 0.86 mmol) dissolved in methanol (2 ml) was added conc. HCl (1 ml). The reaction mixture was stirred for 20 minutes and then concentrated under reduced pressure. Residual HCl was removed by the addition and evaporation of acetonitrile several times. The gum-like hydrochloride salt intermediate was taken up in ethanol (10 ml) and aldehyde 33 (197 mg, 0.66 mmol) added followed by sodium cyanoborohydride (63 mg, 0.99 mmol). The reaction mixture was allowed to stir overnight and then acidified to pH 1 using conc. HCl. A small amount of HCN was evolved at this point. The reaction mixture was absorbed onto silica under reduced pressure and the product purified by flash chromatography (90:10:0.5 CHCl$_3$/MeOH/NEt$_3$) to give 42 as a colourless solid (170 mg, 69%); mp 214-216° C.; $^1$H NMR (300 MHz, CDCl$_3$) δ 8.52 (s, 1H), 7.33 (s, 1H), 7.31-7.20 (m, 5H), 5.70 (s, 2H), 4.45 (s, 2H), 4.09 (s, 3H), 3.97 (d, J=13.5 Hz, 1H), 3.80 (d, J=13.5 Hz, 1H), 3.68 (br s, 1H), 3.55-3.46 (m, 1H), 3.45-3.42 (m, 2H), 3.34 (ddd, J=8.8, 6.9, 2.5 Hz, 1H), 3.01 (ddd, J=8.7, 8.7, 7.3 Hz, 1H), 2.14-2.00 (m, 1H), 1.90 (dddd, J=10.1, 8.1, 8.1, 2.4 Hz, 1H); $^{13}$C NMR (75 MHz, CDCl$_3$) δ 156.2, 149.9, 149.8, 136.7, 131.5, 128.3, 127.8, 127.5, 115.8, 114.0, 76.8, 70.0, 66.6, 64.0, 53.5, 51.3, 50.6, 18.7; HRMS calcd for (M+H$^+$, ESI) C$_{20}$H$_{25}$N$_4$O$_3$: 369.1927; found: 369.1948.

(±)7-((2-(Hydroxymethyl)azetidin-1-yl)methyl)-5H-pyrrolo[3,2-d]pyrimidin-4-ol (43). A solution of azetidine 42 (68 mg, 0.18 mmol) was heated to reflux in conc. HCl (3 ml) for 2 hours. The mixture was concentrated under reduced pressure and then azeotropically dried by the addition and evaporation of acetonitrile. The residue was purified by flash chromatography on silica (65:35:7:1, CHCl$_3$/MeOH/H$_2$O/NH$_4$OH) to give 21 as an amorphous white solid (33 mg, 76%); mp 213-216° C.; HPLC purity 98.9%, 220 nm (Synergi™ Polar-RP, 0:100 to 100:0 MeOH/0.1% TFA in H$_2$O over 30 minutes); $^1$H NMR (300 MHz, 60:40 CD$_4$OD/D$_2$O) δ 8.03 (s, 1H), 7.60 (s, 1H), 4.23 (d, J=13.8 Hz, 1H), 4.08 (d, J=13.5 Hz, 1H), 4.10-3.98 (m, 1H), 3.65-3.49 (m, 4H), 2.27-2.11 (m, 2H); $^{13}$C NMR (75 MHz, 60:40 CD$_4$OD/D$_2$O) δ 156.1, 144.9, 143.6, 130.8, 118.7, 109.9, 68.3, 63.4, 51.1, 49.4, 20.0; HRMS calcd for (M+H, ESI) C$_{11}$H$_{15}$N$_4$O$_2$: 235.1195; Found: 235.1196.

Enzyme Inhibition Assays

For PNP assays, inosine and inhibitor concentrations were determined spectrophotometrically using an ε$_{260}$ of 7.1 mM$^{-1}$ cm$^{-1}$ (pH 6) [Dawson' et al, *Data for Biochemical Research*, 3rd ed., 1986, Clarendon Press, Oxford, U.K.] and an ε$_{261}$ of 9.54 mM$^{-1}$ cm$^{-1}$ (pH 7) [Lim, M.-I.; Ren, Y.-Y.; Otter, B. A.; Klein, R. S., *J. Org. Chem.* 1983, 48, 780-788], respectively. For MTAN/MTAP assays, methylthioadenosine and inhibitor concentrations were determined using an ε$_{260}$ of 14.9 mM$^{-1}$ cm$^{-1}$ (pH 6) [Dawson et al, as above] and an ε$_{275}$ of 8.5 mM$^{-1}$ cm$^{-1}$ (pH 7), [*J. Org. Chem.* 1983, 48, 780-788] respectively. PNP and MTAN/MTAP activities were monitored by xanthine oxidase coupled assays, as previously described [*Biochemistry*, 2006, 45, 12929-12941; *Biochemistry*, 1998, 37, 8615-8621]. In all cases, the inhibitor concentration was at least 10-fold greater than the enzyme concentration, as required for simple analysis of slow-onset tight-binding inhibition [Morrison, J. F.; Walsh, C. T. *Adv. Enzymol. Relat. Areas Mol. Biol.*, 1988, 61, 201-301] Michaelis constants used in data fitting were as follows: 40 μM, 34 μM, and 5 μM for inosine with human, bovine, and *P. falciparum* PNPs, respectively; 5 μM, 0.43 μM, and 23 μM for MTA with human MTAP, *E. coli* MTAN, and *S. pneumoniae* MTAN, respectively.

Biological Data

TABLE 1

Inhibition constants for the interaction of Immucillins with a variety of PNPs.[a]

| Compound | Human PNP (nM) | Bovine PNP (nM) | P. falciparum PNP (nM) |
|---|---|---|---|
| 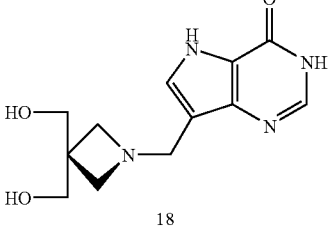<br>18 | $K_i = 0.229 \pm 0.015$ | $K_i = 0.065 \pm 0.06$<br>$K_i^* = 0.236 \pm 0.003$ | $K_i > 10,000$ |
| 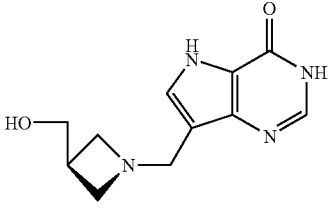<br>19 | $K_i = 6.3 \pm 1.1$ | $K_i = 4.8 \pm 0.3$ | $K_i > 10,000$ |
| 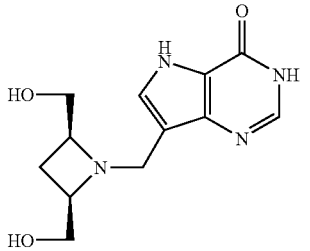<br>36 | $K_i = 12.9 \pm 0.3$ | $K_i = 16 \pm 3$ | $K_i = 1,290 \pm 30$ |
| 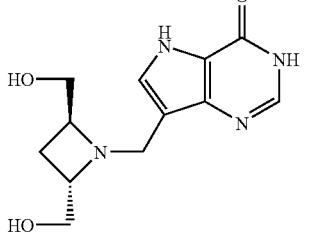<br>(±)-37 | $K_i = 280 \pm 40$ | $K_i = 360 \pm 40$ | $K_i = 580 \pm 30$ |
| 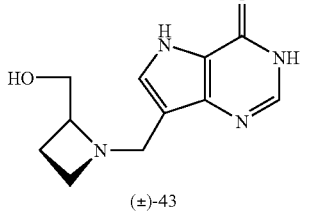<br>(±)-43 | $K_i = 1.8 \pm 0.3$<br>$K_i^* = 0.260 \pm 0.02$ | $K_i = 1.8 \pm 0.2$ | $K_i = 191 \pm 11$ |

[a]$K_i^*$ is the dissociation constant for E + I ⇌ EI*. In cases where only $K_i$ is reported, no slow-onset inhibition was observed.

TABLE 2

Inhibition constants for the interaction of Azetidine Immucillins with MTAP and MTANs.[a]

| Compound | Human MTAP (nM) | E. coli MTAN (nM) | S. pneumoniae MTAN (nM) |
|---|---|---|---|
| 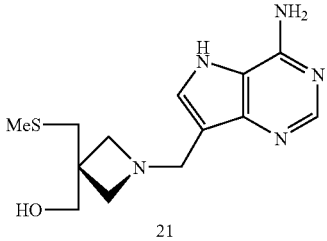 21 | $K_i = 140 \pm 7$ | $K_i = 0.84 \pm 0.09$ | $K_i = 150 \pm 12$ |
| 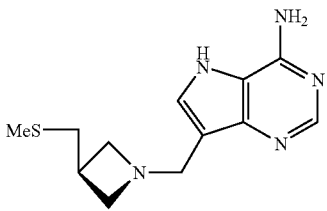 22 | $K_i = 2.0 \pm 0.1$ | $K_i = 0.45 \pm 0.05$ | $K_i = 84 \pm 6$ |

[a]$K_i^*$ is the dissociation constant for E + I ⇌ EI*. In cases where only $K_i$ is reported, no slow-onset inhibition was observed.

Although the invention has been described by way of example, it should be appreciated that variations or modifications may be made without departing from the scope of the invention. Furthermore, when known equivalents exist to specific features, such equivalents are incorporated as if specifically referred to in the specification.

INDUSTRIAL APPLICABILITY

The azetidine analogues of Immucillins and DAD-Me-Immucillins of the invention are potential or actual inhibitors of at least one of PNP, PPRT, MTAP and MTAN, which means they are useful as possible therapeutic agents for treating diseases or conditions such as cancer, bacterial infection, parasitic infection, or a T-cell mediated diseases.

The invention claimed is:
1. A compound of formula (I):

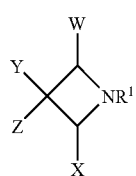

wherein:
W and X are each independently selected from hydrogen, CH$_2$OH, CH$_2$OQ and CH$_2$SQ;
Y and Z are each independently selected from hydrogen, halogen, CH$_2$OH, CH$_2$OQ, CH$_2$SQ, SQ, OQ and Q;
Q is an alkyl, aralkyl or aryl group each of which may be optionally substituted with one or more substituents selected from hydroxy, halogen, methoxy, amino, or carboxy;
R$^1$ is a radical of the formula (II)

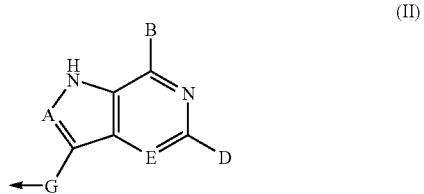

A is selected from CH and CR$^2$, where R$^2$ is selected from halogen, alkyl, aralkyl, aryl, OH, NH$_2$, NHR$^3$, NR$^3$R$^4$ and SR$^5$, where R$^3$, R$^4$ and R$^5$ are each alkyl, aralkyl or aryl groups optionally substituted with hydroxy or halogen, and where R$^2$ is optionally substituted with hydroxy or halogen when R$^2$ is alkyl, aralkyl or aryl;
B is selected from hydroxy, NH$_2$, NHR$^6$, SH, hydrogen and halogen, where R$^6$ is an alkyl, aralkyl or aryl group optionally substituted with hydroxy or halogen;
D is selected from hydroxy, NH$_2$, NHR$^7$, hydrogen, halogen and SCH$_3$, where R$^7$ is an alkyl, aralkyl or aryl group optionally substituted with hydroxy or halogen;
E is N;
G is a C$_{1-4}$ saturated or unsaturated alkyl group optionally substituted with hydroxy or halogen;
or a tautomer thereof, or a pharmaceutically acceptable salt thereof, or an ester thereof.

2. A compound as claimed in claim 1 where W is CH$_2$OH or CH$_2$SQ.

3. A compound as claimed in claim 2 where W is CH$_2$SCH$_3$.

4. A compound as claimed in claim 1 where X is CH$_2$OH or CH$_2$SQ.

5. A compound as claimed in claim 4 where W is CH$_2$SCH$_3$.

6. A compound as claimed in claim 1 where Z is selected from hydrogen, halogen, CH$_2$OH, CH$_2$OQ and CH$_2$SQ.

7. A compound as claimed in claim 6 where Y or Z is CH₂OH.

8. A compound as claimed in claim 6 where Y or Z is CH₂SQ or CH₂OQ.

9. A compound as claimed in claim 1 where either or both of Y or Z is Q.

10. A compound as claimed in claim 6 where either or both of Y or Z is CH₂OH.

11. A compound as claimed in claim 1 where W and X are both hydrogen.

12. A compound as claimed in claim 11 where either or both of Y or Z is CH₂OH.

13. A compound as claimed in claim 11 where either or both of Y or Z is CH₂SQ.

14. A compound as claimed in claim 1 where Y and Z are both hydrogen.

15. A compound as claimed in claim 1 where G is CH₂.

16. A compound as claimed in claim 1 where B is hydroxy or NH₂.

17. A compound as claimed in claim 1 where A is CH.

18. A compound as claimed in claim 1 where D is H or NH₂.

19. A compound as claimed in claim 1 where, when any of Y, Z, B and D is halogen, each halogen is independently chlorine or fluorine.

20. A compound as claimed in claim 1 which is selected from the following:
   i. 7-((2,4-bis(hydroxymethyl)azetidin-1-yl)methyl)-3H-pyrrolo[3,2-d]pyrimidin-4(5H)-one;
   ii. 7-((3,3-bis(hydroxymethyl)azetidin-1-yl)methyl)-3H-pyrrolo[3,2-d]pyrimidin-4(5H)-one;
   iii. 7-((2-(hydroxymethyl)azetidin-1-yl) methyl)-3H-pyrrolo[3,2-d]pyrimidin-4(5H)-one;
   iv. 7-((3-(hydroxymethyl)azetidin-1-yl)methyl)-3H-pyrrolo[3,2-d]pyrimidin-4(5H)-one;
   v. 7-((3-hydroxy-3-(hydroxymethyl)azetidin-1-yl)methyl)-3H-pyrrolo[3,2-d]pyrimidin-4(5H)-one;
   vi. 7-((3-hydroxy-2-(hydroxymethyl)azetidin-1-yl)methyl)-3H-pyrrolo[3,2-d]pyrimidin-4(5H)-one;
   vii. 2-amino-7-((2,4-bis(hydroxymethyl)azetidin-1-yl)methyl)-3H-pyrrolo[3,2-d]pyrimidin-4(5H)-one;
   viii. 2-amino-7-((3,3-bis(hydroxymethyl)azetidin-1-yl)methyl)-3H-pyrrolo[3,2-d]pyrimidin-4(5H)-one;
   ix. 2-amino-7-((2-(hydroxymethyl)azetidin-1-yl)methyl)-3H-pyrrolo[3,2-d]pyrimidin-4(5H)-one;
   x. 2-amino-7-((3-(hydroxymethyl)azetidin-1-yl)methyl)-3H-pyrrolo[3,2-d]pyrimidin-4(5H)-one;
   xi. 2-amino-7-((3-hydroxy-3-(hydroxymethyl)azetidin-1-yl)methyl)-3H-pyrrolo[3,2-d]pyrimidin-4(5H)-one;
   xii. 2-amino-7-((3-hydroxy-2-(hydroxymethyl)azetidin-1-yl)methyl)-3H-pyrrolo[3,2-d]pyrimidin-4(5H)-one;
   xiii. (1-((4-amino-5H-pyrrolo[3,2-d]pyrimidin-7-yl)methyl)-3-(methylthiomethyl)azetidin-3-yl)methanol;
   xiv. 1-((4-amino-5H-pyrrolo[3,2-d]pyrimidin-7-yl)methyl)-3-(methylthiomethyl)azetidin-3-ol;
   xv. (1-((4-amino-5H-pyrrolo[3,2-d]pyrimidin-7-yl)methyl)-4-(methylthiomethyl)azetidin-2-yl)methanol;
   xvi. 7-((2-(methylthiomethyl)azetidin-1-yl)methyl)-5H-pyrrolo[3,2-d]pyrimidin-4-amine;
   xvii. 7-((3-(methylthiomethyl)azetidin-1-yl)methyl)-5H-pyrrolo[3,2-d]pyrimidin-4-amine; or
   xviii. 1-((4-amino-5H-pyrrolo[3,2-d]pyrimidin-7-yl)methyl)-2-(methylthiomethyl)azetidin-3-ol.

21. A pharmaceutical composition comprising a compound of claim 1 and a pharmaceutically effective excipient, diluent or carrier.

22. A pharmaceutical composition comprising a compound of claim 20 and a pharmaceutically effective excipient, diluent or carrier.

* * * * *